United States Patent [19]

Sandhaus

[11] Patent Number: 5,067,958
[45] Date of Patent: Nov. 26, 1991

[54] APPARATUS FOR EFFECTING OCCLUSION OF TARGET VESSELS OR TISSUE

[75] Inventor: Jeffrey J. Sandhaus, Snedens Landing, N.Y.

[73] Assignee: The Population Counsil, Inc., New York, N.Y.

[21] Appl. No.: 608,297

[22] Filed: Nov. 2, 1990

Related U.S. Application Data

[63] Continuation-in-part of Ser. No. 326,299, Mar. 21, 1989, Pat. No. 4,967,949, which is a continuation-in-part of Ser. No. 884,417, Jul. 11, 1986, abandoned.

[51] Int. Cl.$^5$ .............................................. A61B 17/00
[52] U.S. Cl. .................................... 606/142; 606/139; 606/143; 227/19
[58] Field of Search ................... 606/142, 139, 143; 227/19, 901

[56] References Cited

U.S. PATENT DOCUMENTS

| | | | |
|---|---|---|---|
| 3,999,555 | 12/1976 | Person | 606/151 |
| 4,201,314 | 5/1980 | Samuels | 601/151 |
| 4,299,224 | 11/1981 | Noiles | 606/143 |
| 4,380,238 | 4/1983 | Colucci et al. | 606/135 |
| 4,394,864 | 7/1983 | Sandhaus | 606/142 |
| 4,430,997 | 2/1984 | DiGioranni | 606/143 |
| 4,448,193 | 5/1984 | Ivanov | 606/143 |
| 4,450,840 | 5/1984 | Mericle et al. | 606/143 |
| 4,452,376 | 6/1984 | Klieman et al. | 606/142 |
| 4,478,218 | 10/1984 | Mericle | 606/143 |
| 4,616,651 | 10/1986 | Golden | 606/142 |
| 4,635,634 | 1/1987 | Santos | 606/142 |
| 4,674,504 | 6/1987 | Klieman et al. | 606/143 |
| 4,929,240 | 5/1990 | Kirsch et al. | 606/151 |

Primary Examiner—Stephen C. Pellegrino
Assistant Examiner—Gary Jackson
Attorney, Agent, or Firm—Lerner, David, Littenberg, Krumholz & Mentlik

[57] ABSTRACT

Apparatus for implanting closable locking clips to effect the percutaneous occlusion of target vessels or tissue is disclosed, including a pair of pivotable jaws defining a clip retaining cavity, a clip moving slide for sliding a locking clip from a retracted position remote from the clip retaining cavity to an actuated position with the clip retaining cavity, and a camming surface operatively disposed within the clip retaining cavity so that upon slidable movement of the locking clip from the retracted position to the actuated position the camming surface causes at least partial closure of the locking clip therein.

12 Claims, 25 Drawing Sheets

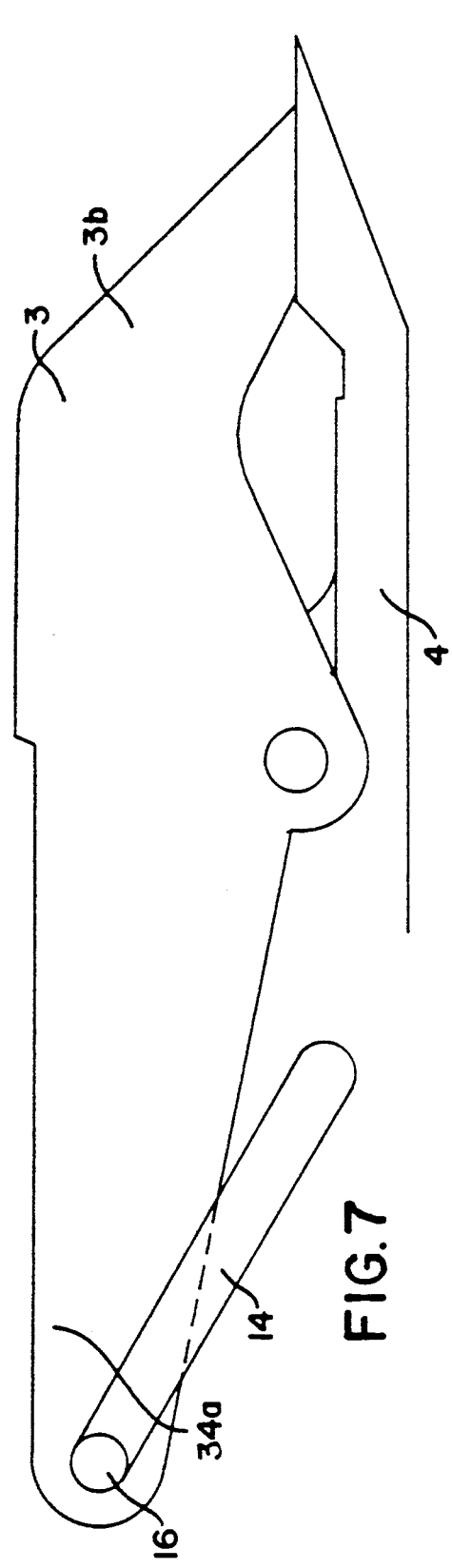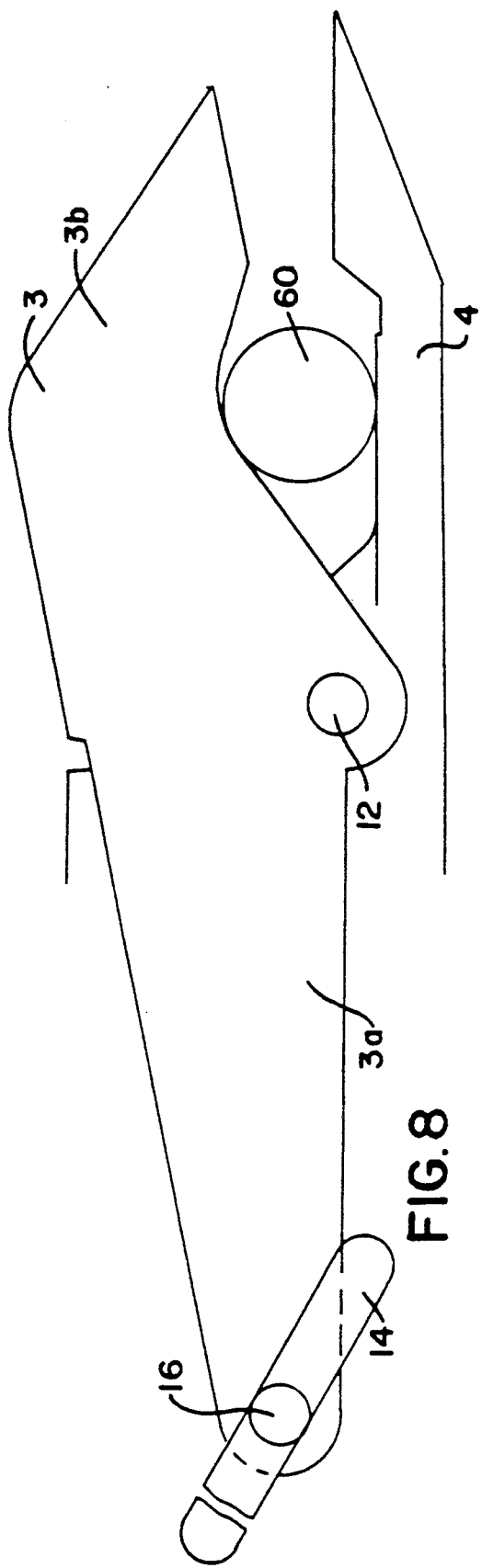

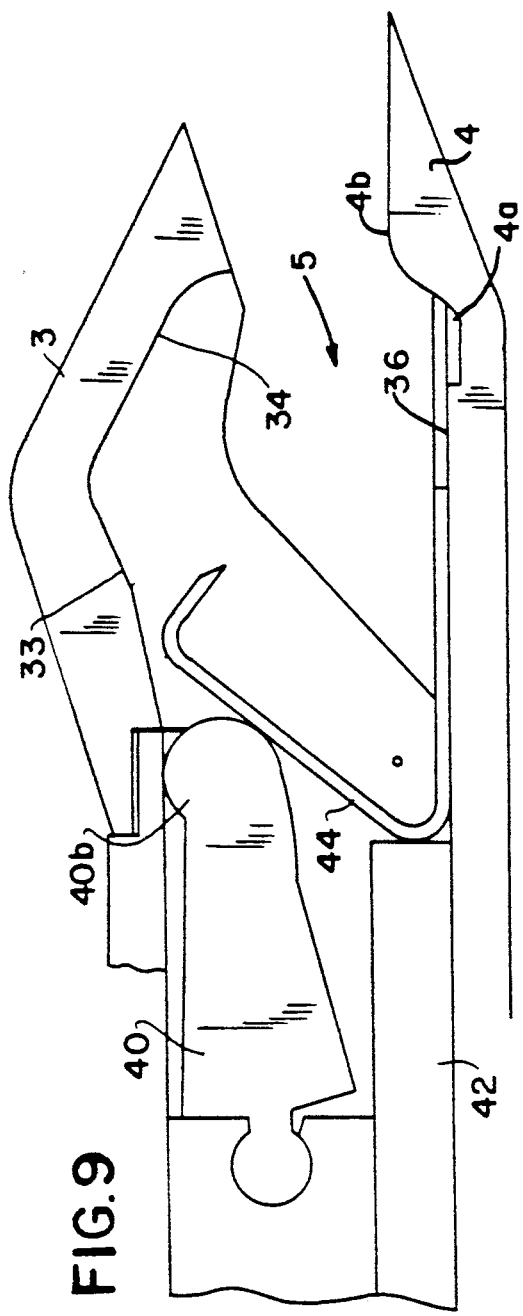
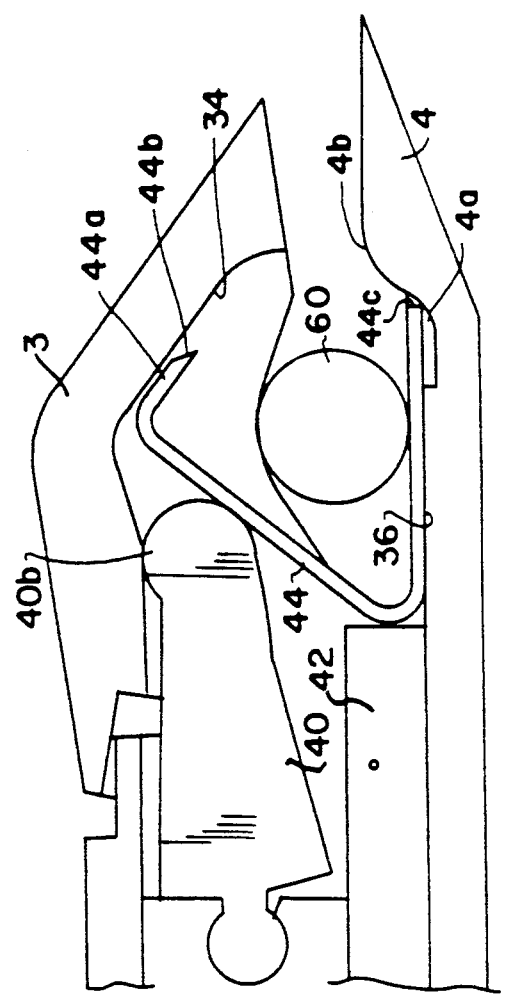

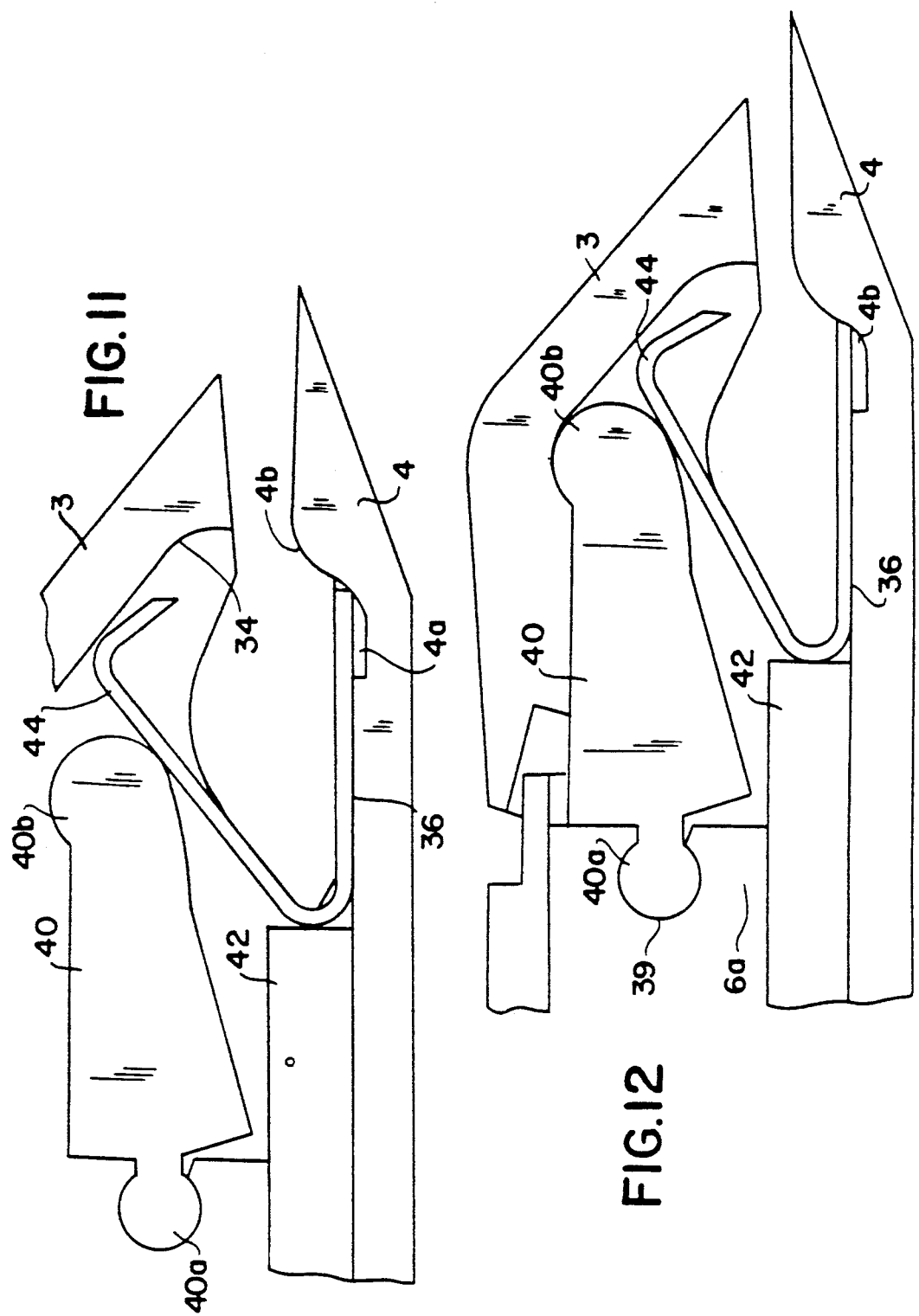

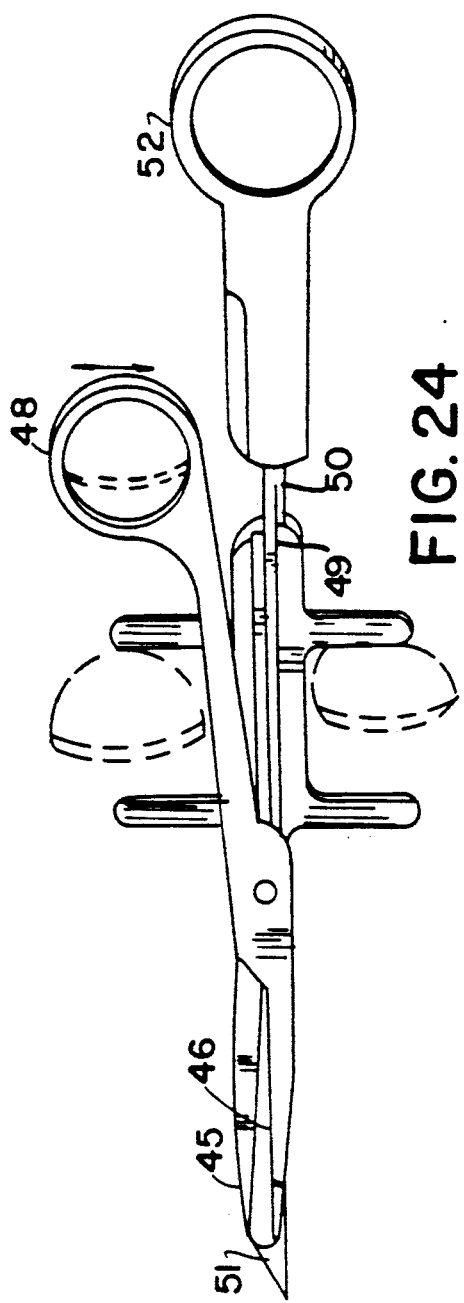
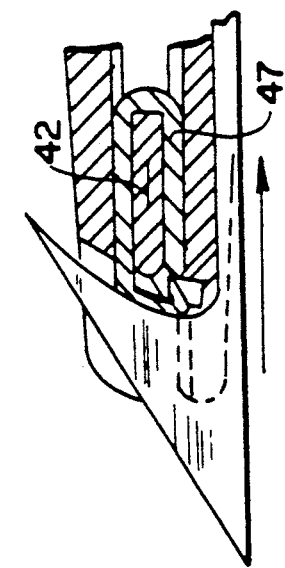
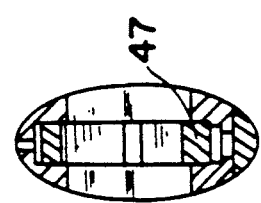
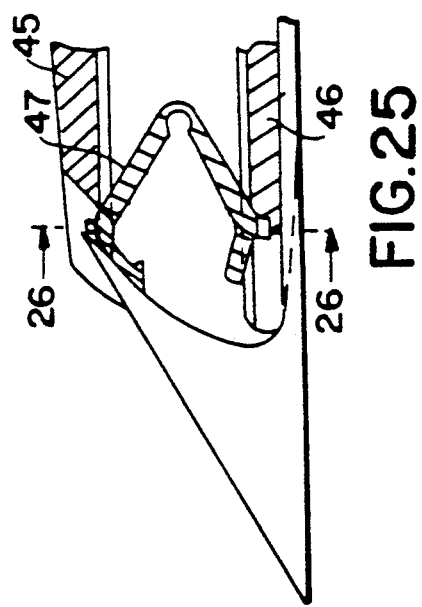
FIG. 24
FIG. 27
FIG. 26
FIG. 25

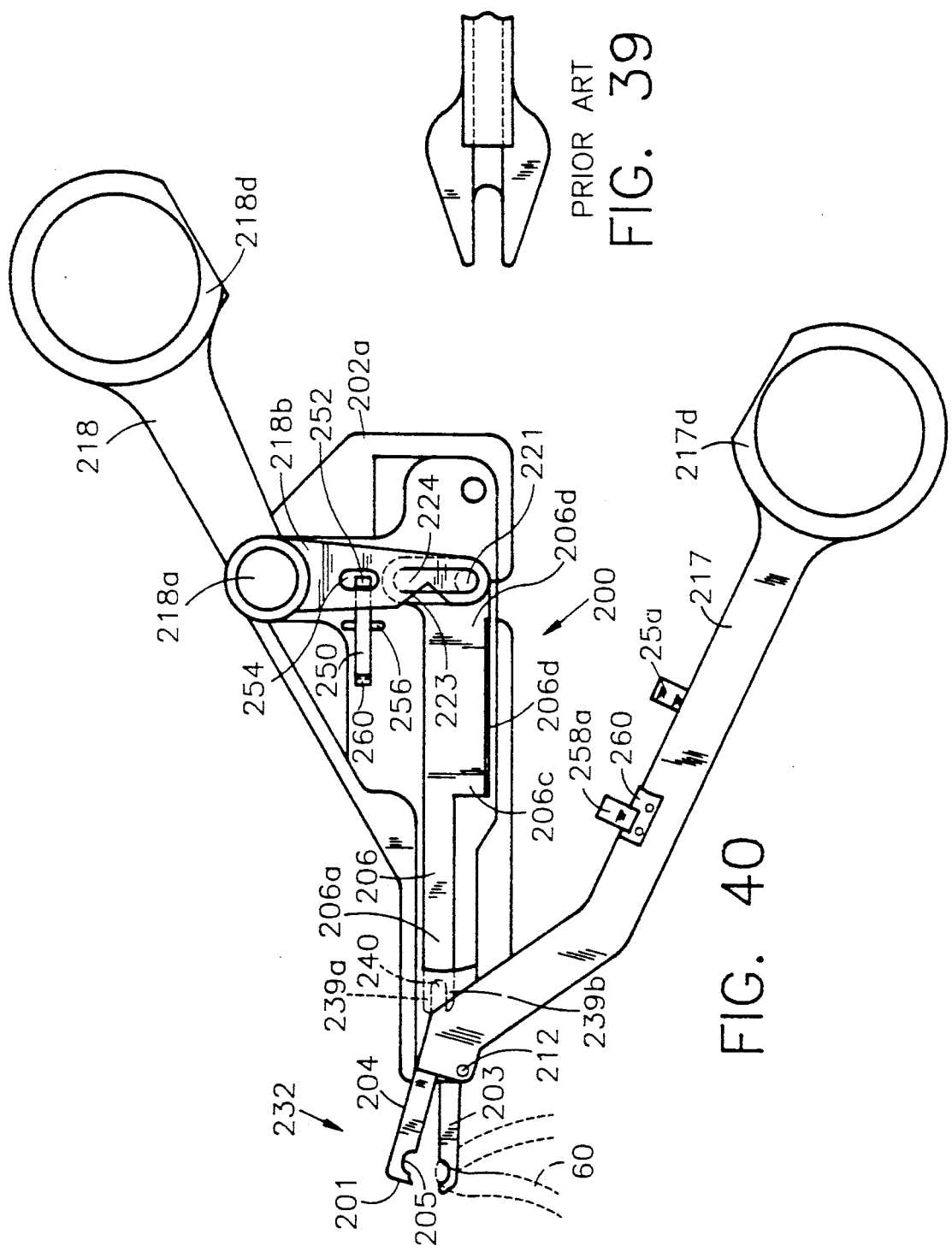

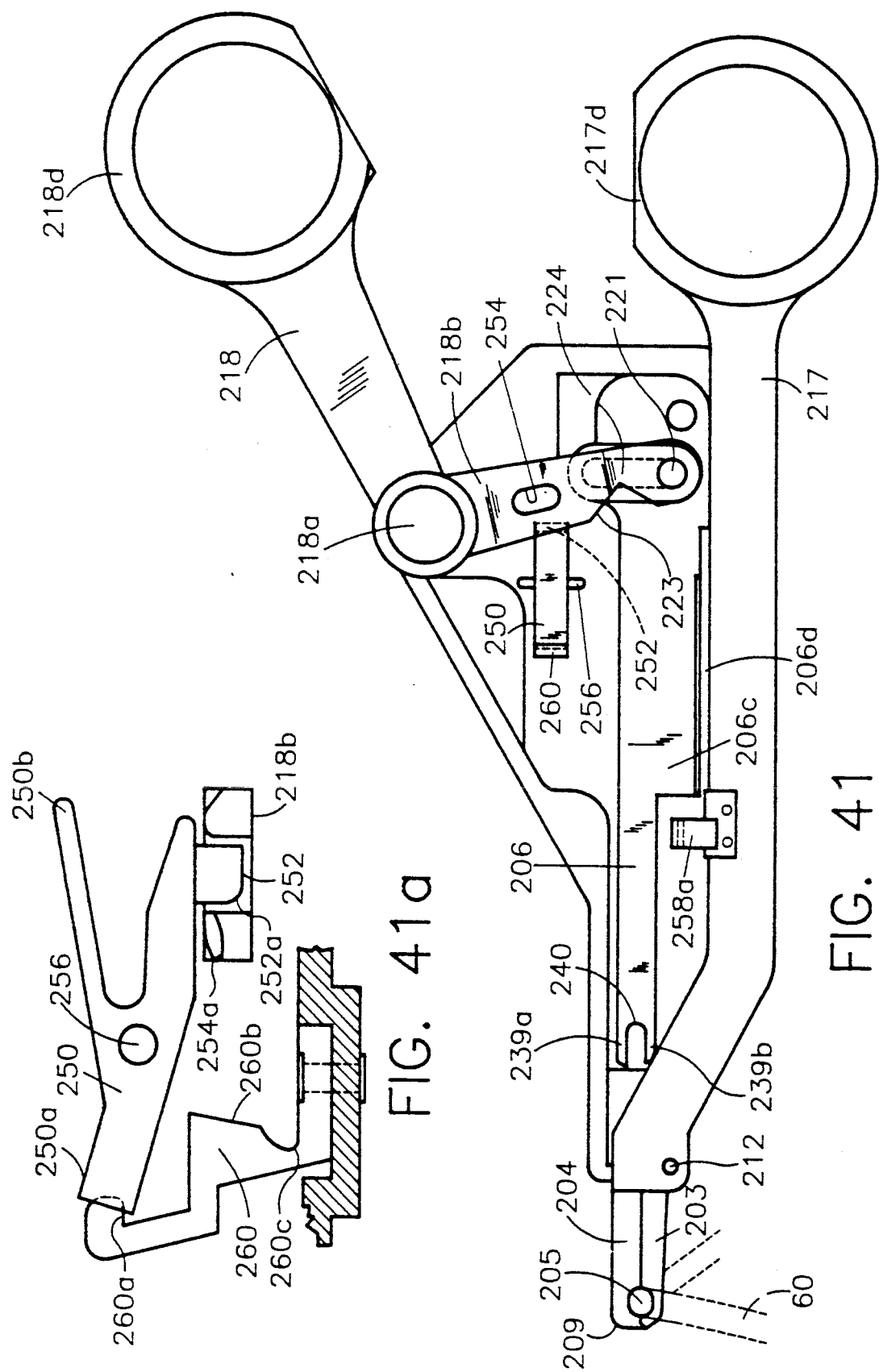

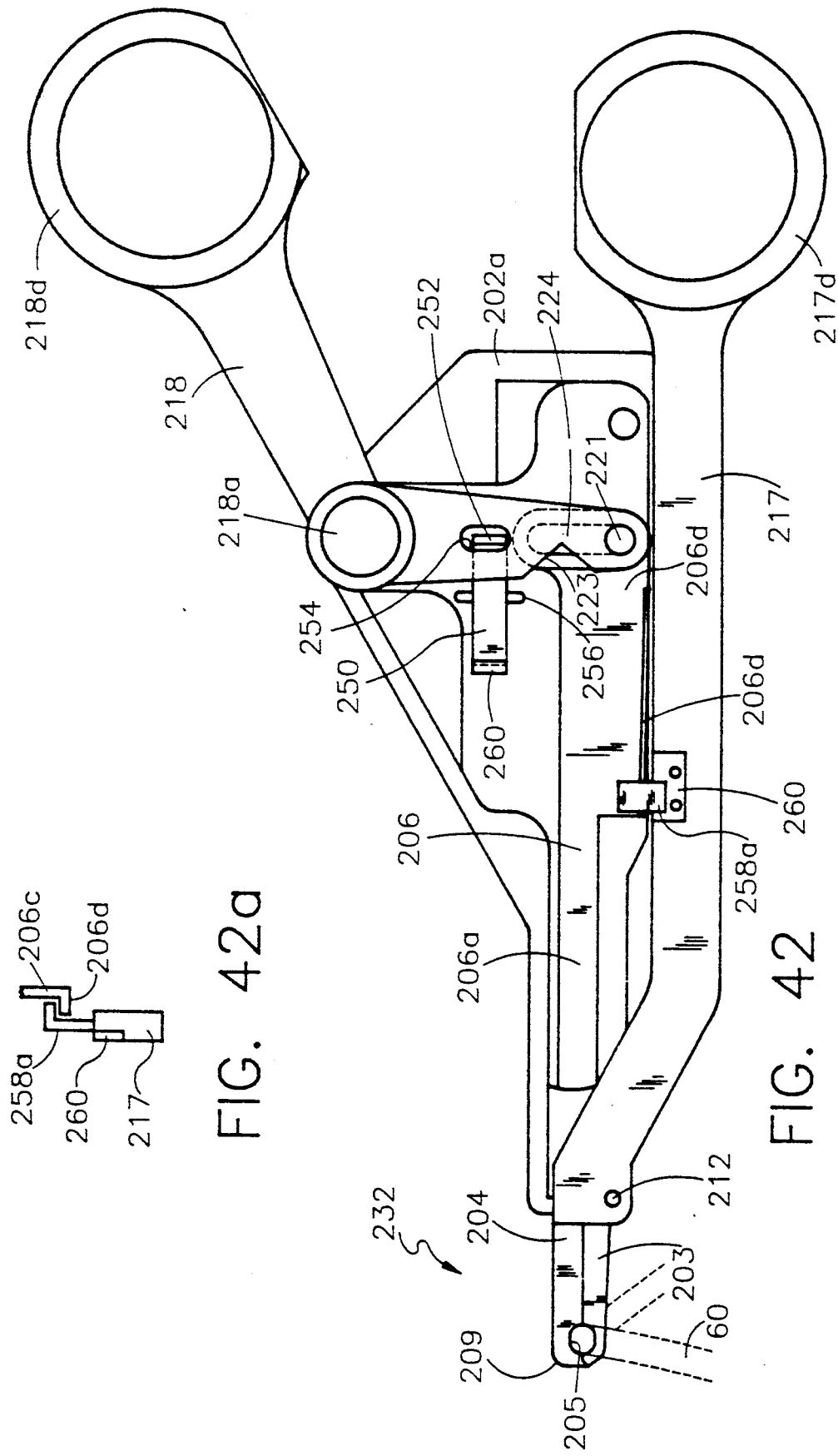

APPARATUS FOR EFFECTING OCCLUSION OF TARGET VESSELS OR TISSUE

CROSS-REFERENCES TO RELATED APPLICATIONS

The present application is a continuation-in-part of application Ser. No. 07/326,299, now U.S. Pat. No. 4,967,949 filed on Mar. 21, 1989, which, in turn, is a continuation-in-part of application Ser. No. 06/884,417 filed on July 11, 1986, now abandoned.

FIELD OF THE INVENTION

The present invention relates to apparatus for the operative occlusion of target vessels in a patient. More particularly, the present invention relates to apparatus for occluding the vas deferens during a vasectomy. Still more particularly, the present invention relates to apparatus for implanting disposable clips to effect the occlusion of targeted tissue or target vessels such as the vas deferens.

BACKGROUND OF THE INVENTION

The procedures which are currently employed for the occlusion of target vessels during surgical procedures such as laproscopies include the attachment of clips to these vessels with clip applying devices which can be extended into the target area and then, by means of external triggers, close a pair of jaws for the purpose of closing the clip onto the target vessel.

Conventional clip application requires the surgical exposure and 360° isolation of the intended vessel (or targeted structure). This requires careful and accurate dissection in order to insure proper placement and secure clip engagement. As shown in FIG. 39, the vessel is then positioned well within the opened jaw members of this prior art device, so that U-or V-shaped clip can be applied with any degree of assurance that its distal arms will meet for successful engagement. The jaw members of the instrument thus remain parallel to each other upon closure, and thereby perform the crimping action for clip application. A serious problem with these devices relates to the fact that in real environments there are any number of impediments to adequate vessel mobilization. It is therefore necessary in many cases to carry out precise clamping and ligation.

The conventional clip application method has been applied to therapeutic laproscopies. Thus, endoscopic devices have been widely applied to abdominal procedures, such as cholecystectomy, appendectomy, and lysis of intestinal adhesions. Endo-cholecystectomy, for example, requires clip ligation of the cystic duct and cystic artery. Meticulous dissection can be tedious, especially in the presence of inflamed tissues. In any event, the prior techniques and devices have not satisfactorily afforded accurate ductal and vascular control, along with the assurance of precision clip application.

The procedure which is generally employed in connection with simple vasectomies includes grasping the vas deferens with an appropriate instrument and making an incision to the adjacent subcutaneous tissue. The vasal sheath is then grasped with a clamp and incised with the vas being dissected from the sheath. The vas is then isolated and a segment is excised whereupon the distal end of the vas is electrocoagulated and/or ligated and then buried within the vasal sheath. The proximal end of the vas is also electrocoagulated and/or ligated, and finally the skin can be closed.

Although the latter procedure has proven to be quite reliable, it is the subject of a number of disadvantages. In particular, this above-described procedure is relatively time-consuming, requiring on the order of at least about 40 minutes or so. The conventional procedure thus requires a surgical incision, entailing all of the necessary precautions normally incident to relatively complicated surgical procedures.

Procedures for the percutaneous occlusion of the vas deferens in a vasectomy have thus been generated in which a mechanical clip is applied to the vas deferens as taught forth in U.S. Pat. No. 4,394,864, in the name of the inventor in the present application. This patent discloses an apparatus and method for effecting occlusion of the vas deferens including a pair of pivotally coupled jaws for receiving a U-shaped locking clip therein, so that after the locking clip is placed between the jaws, closure of the jaws entirely effects closure of the locking clip therein. Although this apparatus has provided a major improvement in the performance of such vasectomies, it relies entirely upon the pivoting of the jaw members to effect the closure of the clip, a movement which is not always desirable in such surgical procedures. The search has therefore continued for improved devices to eliminate this shortcoming and further facilitating both the vasectomy procedure, and the general use of such procedures for laproscopies.

SUMMARY OF THE INVENTION

In accordance with the present invention, it has now been discovered that the foregoing and other shortcomings can be obviated by applicant's discovery of an apparatus for implanting a closable clip to effect the occlusion of a target vessel which includes first and second jaw members relatively movable between open and closed positions and defining a clip retaining cavity therebetween, the clip retaining cavity having sufficient size to accommodate the clip therein, and clip closure means for moving the clip from a retractable position (remote from the clip retaining cavity) to an actuating position (within the clip retaining cavity), and means for causing at least a partial closure of the clip.

In accordance with one embodiment of the apparatus of the present invention, camming means are disposed within the clip retaining cavity for assisting in the at least partial closure of the clip. Preferably, the camming means are associated with at least one of the first and second jaw members, and preferably both of said first and second jaw members.

In accordance with another embodiment of the apparatus of the present invention, the clip closure means comprises a slidable pusher member including a first end proximate to the clip retaining cavity and a second end distal from the clip retaining cavity. In a preferred embodiment, the clip closure means includes pivotable handle means having a first end distal from the second end of the slidable pusher member and a second end proximate to the second end of the slidable pusher member and in contact therewith, the pivotable handle means being pivotable about a point intermediate the first and second ends of the pivotable handle means whereby pivoting of the pivotable handle means results in longitudinal displacement of the slidable pusher member.

In a highly preferred embodiment, the slidable pusher member includes groove means substantially transverse to the direction defined by the longitudinal displacement of the slidable pusher member and the pivotable handle means includes grooved follower means.

In accordance with another embodiment of the apparatus of the present invention, one of the first and second jaw members includes an inner surface defining a portion of the clip retaining cavity and the camming means comprises an angularly displaced wall surface on the inner surface of that one of the first and second jaw members.

In accordance with another embodiment of the apparatus of the present invention, the first jaw member remains stationary and the second jaw member is pivotable, including second jaw member pivot means for pivoting the second jaw member between the open and closed positions. In a preferred embodiment, the second jaw pivot means comprises a second jaw handle member, and preferably the second handle member locking means are provided for locking the second handle member in the closed position.

In accordance with another embodiment of the apparatus of the present invention, the first and second jaw members define a smooth outer surface, and preferably the first and second jaw members combine to define an opening at the distal end therebetween which substantially duplicates the occlusion of the target vessel by the clip when the clip is closed thereon.

BRIEF DESCRIPTION OF THE DRAWINGS

A more complete appreciation of the subject matter of the present invention and the various advantages thereof can be realized by reference to the following detailed description, in which reference is made to the accompanying drawings in which:

FIG. 7 is a top, plan, exploded, partial view of the upper and lower jaws of the apparatus shown in FIG. 1 in the entry position;

FIG. 8 is a top, plan, exploded view of the upper and lower jaws of the apparatus shown in FIG. 1 in connection with the vas deferens captured therein;

FIG. 9 is top, plan, enlarged view of the upper and lower jaws of the apparatus shown in FIG. I with the jaws open and the locking clip in retracted position therein;

FIG. 10 is a top, plan, enlarged view of the upper and lower jaws of the apparatus shown in FIG. 1 with the locking clip in the advanced position;

FIG. 11 is a top, plan, enlarged view of the upper and lower jaws of the apparatus shown in FIG. 1 with the pusher member in an advanced position initiating closure of the locking clip therein;

FIG. 12 is a top, plan, enlarged view of the upper and lower jaws of the apparatus shown in FIG. 1 with the pusher member in an intermediate forward position and the locking clip further closed thereby;

FIG. 24 is a perspective view of another embodiment of the apparatus in accordance with the present invention;

FIG. 25 is a top, plan, partially sectional view of a portion of the apparatus of FIG. 24;

FIG. 26 is a front, sectional view of the apparatus of FIG. 25, taken along section 26—26 thereof;

FIG. 27 is a top, plan, partially sectional view of the portion of the apparatus shown in FIG. 25, with the clip closed thereby;

FIG. 39 is a top, partial, perspective view of a clip applicating laproscope device of the prior art;

FIG. 40 is a top, elevational view of the inner mechanism of another embodiment of the apparatus of the present invention;

FIG. 41 is a top, elevational view of the device shown in FIG. 40 with the jaws closed FIG. 41A is a side, partially sectional view of a locking mechanism used in the closure shown in FIG. 41;

FIG. 42 is a top, elevational view of the device shown in FIG. 40, with the clip advancing process initiated;

FIG. 42A is a side, sectional view of a portion of the device shown in FIG. 42;

DETAILED DESCRIPTION

The present invention can be more fully appreciated with reference to the accompanying Figures, in which like numerals refer to like portions thereof.

Figure 16:
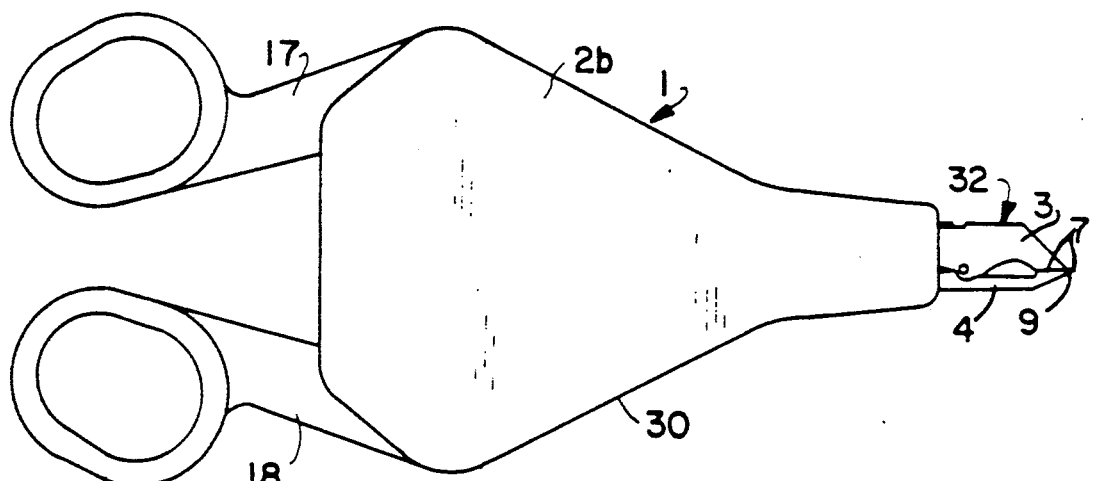
FIG. 16 is a top plan view of the apparatus shown in FIG. 1, wherein the housing cover is in assembled position.
Figure 17:
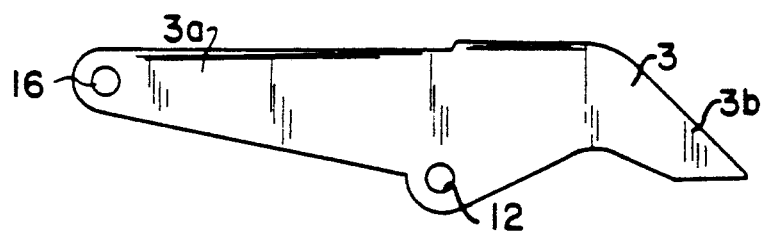
FIG. 17 is a top, plan view of the upper jaw of the apparatus shown in FIG. 1.
Figure 18:
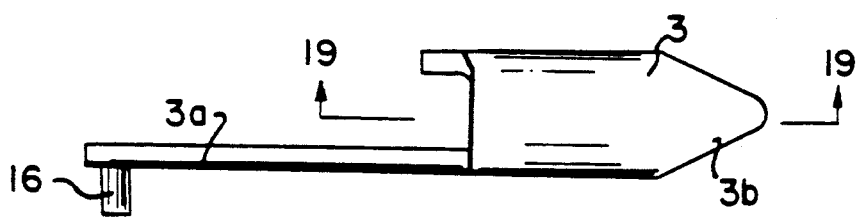
FIG. 18 is a side, elevational view of the upper jaw shown in FIG. 17.
Figure 19:
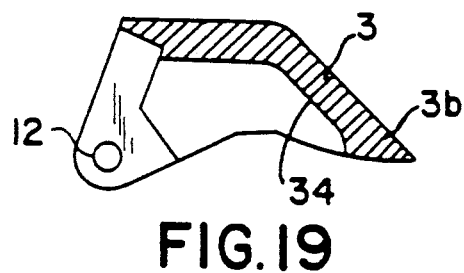
FIG. 19 is a cross-sectional view of the upper jaw taken on line 19—19 of FIG. 18.
Figure 22:
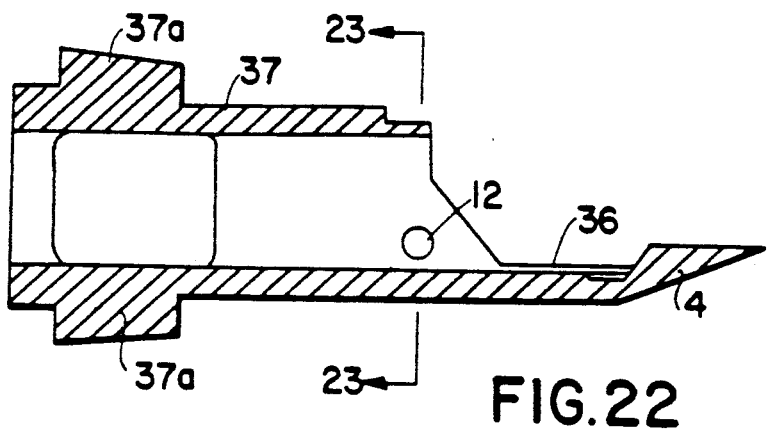
FIG. 22 is a cross-sectional view of the lower jaw taken on line 22—22 of FIG. 21.
Figure 23:
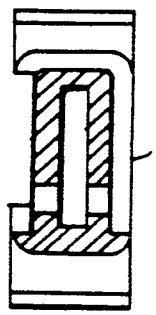
FIG. 23 is a cross-sectional view of the lower jaw taken on line 23—23 of FIG. 22.
Figure 21:
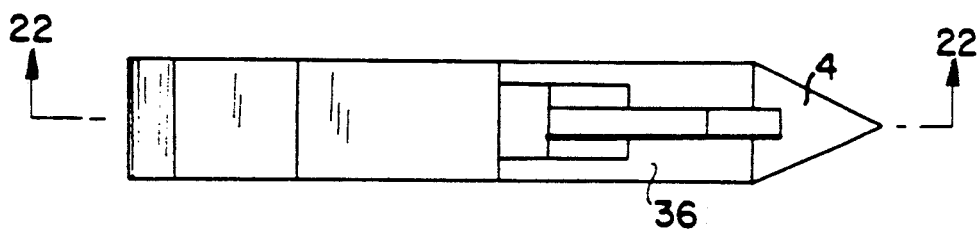
FIG. 21 is a side, elevational view of the lower jaw shown in FIG. 20.
Figure 20:
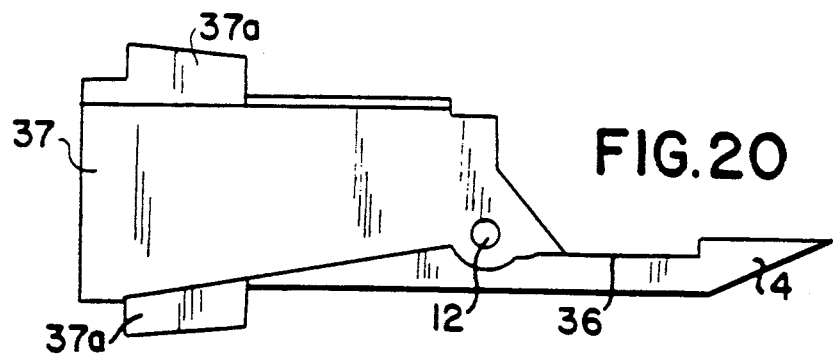
FIG. 20 is a top, plan view of the lower jaw of the apparatus shown in FIG. 1.

The apparatus of the present invention comprises a compact and highly effective device for implanting closable clips in the manner of this invention. The overall apparatus 1 as shown in FIG. 16 includes a body portion 30, a pair of handles 17 and 18, and a front end 32 comprising a pair of jaws 3 and 4 terminating in a trocar-type obturator configuration 7. (See FIG. 16.) However, it should be understand that the use of such a trocar-type obturator configuration is not essential to the apparatus of the present invention. Thus, it is necessary only where, primarily in connection with percutaneous procedures, it is desired to use this configuration to incise tissue. However, for example, in connection with the embodiment of the present invention shown in FIG. 40, the jaws do not terminate in such a trocar-type obturator, but have a smooth, rounded outer surface which is not intended to cut or incise any tissue. This device can thus be employed in more general applications for the occlusion of target vessels, in conjunction with endoscopic procedures or laproscopies, and where the surgical procedures themselves could include the separate incision of tissue, etc. The device shown in FIG. 40 can thus not only be used in a variety of different procedures, but is generally useful in any procedures where it is desired to implant a clip on a target vessel. That device is discussed in more detail below.

Figure 1:
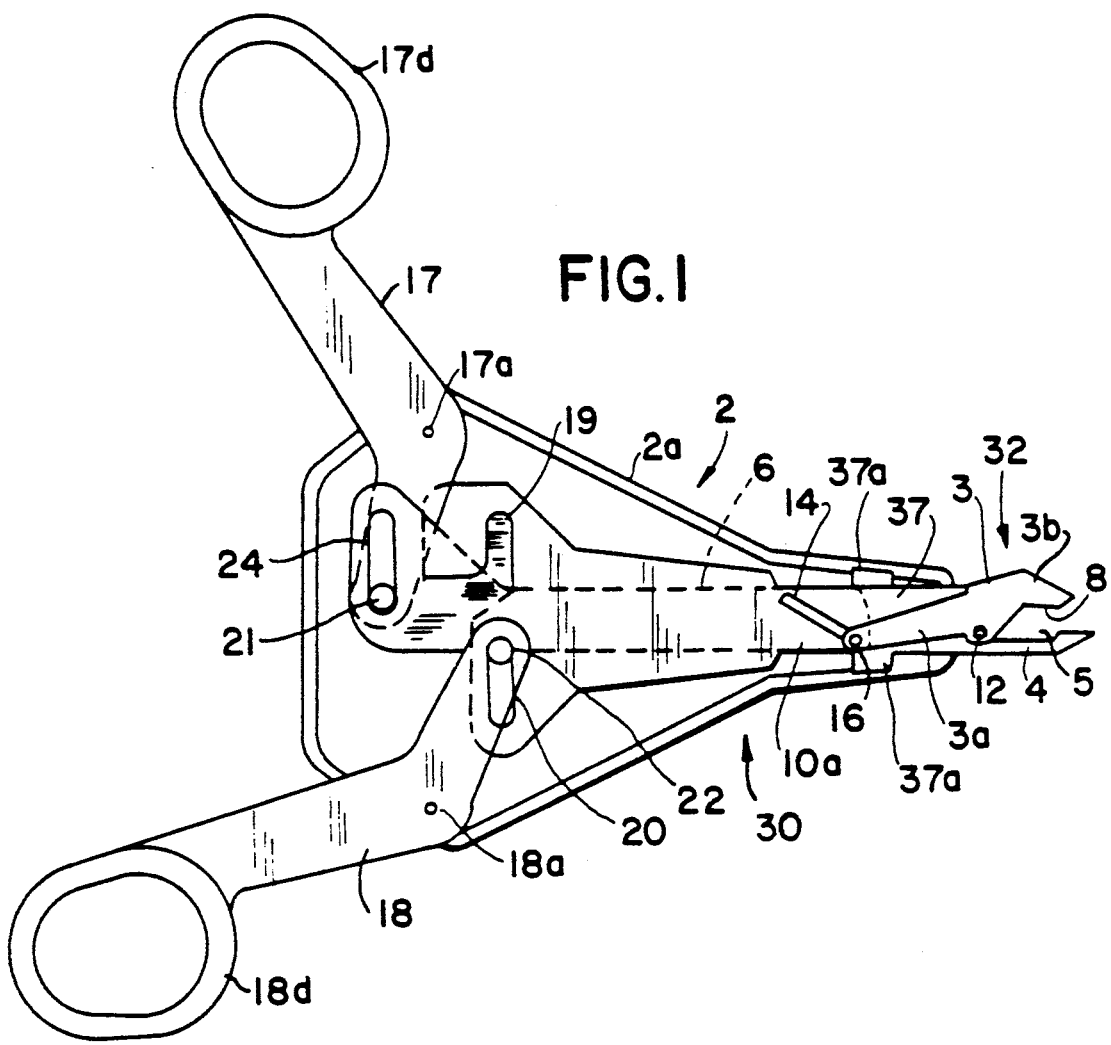
FIG. 1 is a top, plan view of one embodiment of the apparatus in accordance with the present invention, illustrating in particular the inner workings thereof.

Returning to the specific devices shown in FIGS. 1 and 16, the body portion 30 includes two housing portions 2a and 2b, as can be seen in FIGS. 1 and 16 hereof. These two housing halves 2a and 2b can be welded together around the periphery to form housing 2, which includes appropriate openings for the handle members 17 and 18 and the front end 32. The trocar obturator 7 facilitates a variety of functions including penetrating and cutting through tissue, trapping a target vessel, and holding and implanting a clip on a target vessel.

The penetration function thereof is accomplished when the trocar obturator is moved in a forward direction. It is adapted for penetration of tissue by the provision of a barb-shaped end 9 as shown in the Figures. Forward movement of the trocar obturator 7 thus brings the barb-shaped end 9 into contact with the tissue. The pressure resulting from forward movement of the trocar obturator 7 thus effects penetration by pushing the barb-shaped end 9 into the tissue. The remaining functions of the trocar obturator 7 will be more fully appreciated following a detailed description of the trocar obturator 7.

Thus, turning to FIG. 1, the front end 32 of the device of the present invention includes a pair of jaw members 3 and 4 which are pivotably connected at pivot point 12. Upper jaw member 3 and lower jaw member 4 are illustrated in detail in FIGS. 17-19 and FIGS. 20-23, respectively. As shown in FIGS. 9-13 and 17-19, the upper jaw 3 is cup-shaped in form. Thus, the inner surface of the upper jaw 3 includes an inner wall surface comprising a forward camming surface 34 therewithin. As shown in FIGS. 9-13 and 20-23, the lower jaw 4 includes a substantially flat or planar upper surface 36, and therefore upper jaw 3 and lower jaw 4 define a clip retaining cavity 5 therebetween.

Referring specifically to FIGS. 17-23, the configuration of upper jaw 3 and lower jaw 4 and thus the manner in which these jaw members are operatively associated, can be seen. Thus, the rear portion of jaw 3 is telescopically inserted into the passage of jaw 4 (shown in FIG. 23) so that camming surface 34 of jaw 3 is positioned above planar upper surface 36. The jaw members are then connected at pivot point 12.

The lower jaw 4 is intended to remain substantially fixed in the position shown in FIG. 1 so that upon pivoting of the upper jaw 3 about pivot point 12 the jaw can open and close, thus opening and closing the clip retaining cavity 5. In order to maintain the lower jaw 4 in a relatively fixed position the jaw includes a rearwardly extending portion 37 having outwardly extending tabs 37a on either side. These tabs act to fix the lower jaw with respect to the housing portion 2b.

Figure 3:
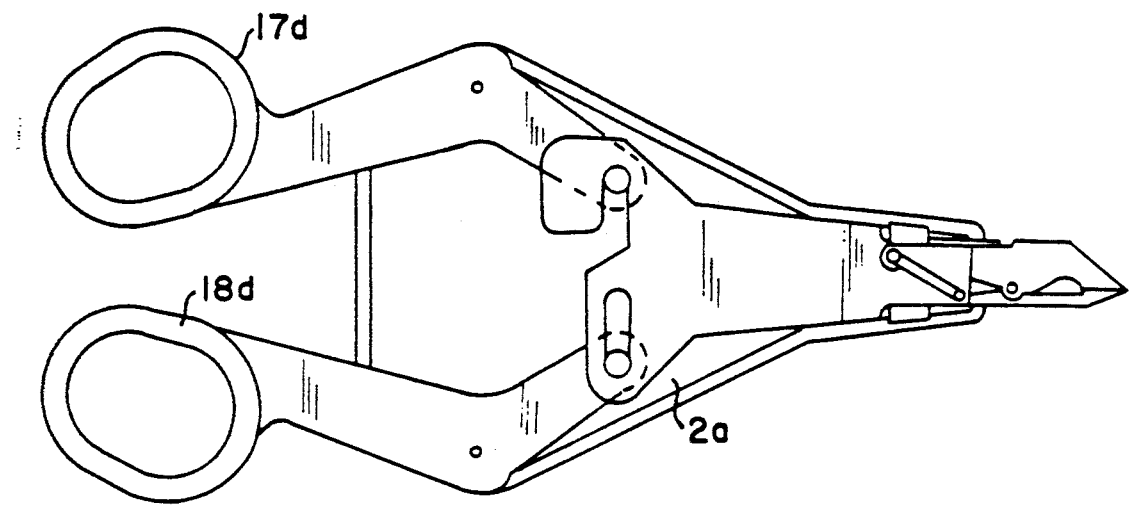
FIG. 3 is a top, plan view of the apparatus shown in FIG. 1, wherein the handle members and the jaw members are shown in the closed position.

Since the upper jaw 3 is pivoted to the lower jaw 4 at pivot point 12, closing of the forward portion of upper jaw 3 is effected by lifting the rear portion 3a thereof. This, in turn, is accomplished by utilization of the moving means or slide 10 which is slidably disposed within the housing 2. Thus, the moving means 10 can slide from a distal position as shown in FIG. 1 remote from the clip retaining cavity, and a proximate position as shown in FIG. 3 adjacent to the clip retaining cavity. The forward end 10a of the moving means 10 adjacent to the jaw members 3 and 4 includes an angularly disposed track 14 extending therethrough. In addition, a track follower 16 extends from the rear portion 3a of the upper jaw 3 into the track 14. Therefore upon sliding motion of the moving means 10 from the position in FIG. 1 to that in FIG. 3, the track follower 16 follows track 14 to raise the rear portion 3a of the upper jaw 3 which pivots about pivot point 12 to close the forward end 3b of the upper jaw 3 towards the fixed lower jaw 4. Thus, when the moving means 10 is in the forward position shown in FIG. 3 the jaws 3 and 4 are in a fully closed position.

The above-described linear reciprocation of the moving means 10 within the housing 2 is effected by the action of handles 17 and 18. More particularly, the rearward end of moving means 10 includes a pair of transverse slots 19 and 20, both of which are shown in FIGS. 1-4. The lower slot 20 is located in an enlarged end portion 10b of the slide 10, while the upper slot 19 is located in an enlarged portion 10c of the slide 10. However, the upper slot 19 is not fully enclosed, and includes an aperture 38 extending rearwardly therefrom. The aperture is thus defined by end portion 10c of the slide 10 and an extending tab portion 10d thereof.

Figure 4:
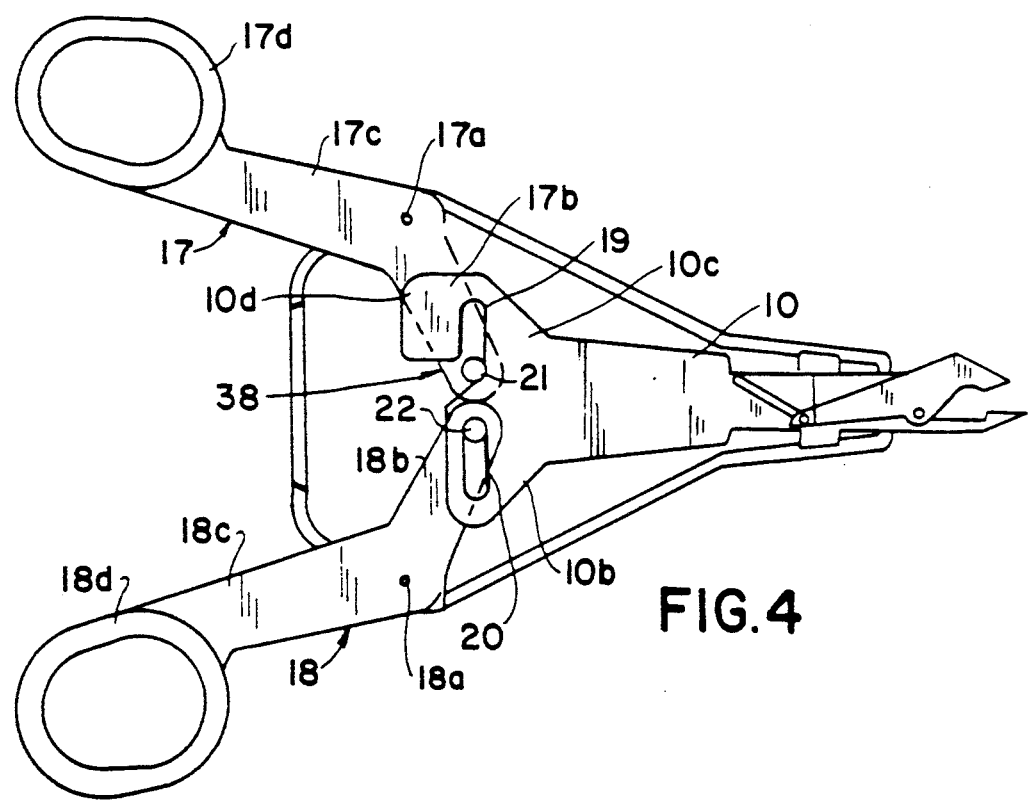
FIG. 4 is a top, plan view of the apparatus shown in FIG. 1, wherein the jaw members are shown in the open position, and handle 17 is shown in a partially closed position.

Turning to handles 17 and 18, handle 17 is pivoted about a pivot point 17a where handle 17 is pivotally connected to housing portion 2b. Handle 17 includes a forward depending leg portion 17b angularly disposed with respect to rearward leg portion 17c which terminates in grip or finger hole 17d. Thus, rotation of the grip 17d about pivot point 17a causes corresponding displacement of the forward portion 17b of the handle 17. Disposed at the forward portion 17b of the handle 17 is a projecting slot follower 21 extending into slot 19. In this manner, rotation of the handle 17 in a downward direction as shown in FIG. 4 causes the slot follower 21 to move upwardly into the position shown in FIG. 3. However, because the slot follower 21 is located below pivot point 17a, the motion of the slot follower 21 is not exclusively transverse with respect to the longitudinal direction of slide 10, but includes a forward longitudinal component directed towards the jaws 3 and 4. This, in turn, causes the slide 10 to move forwardly into the position shown in FIG. 3, at which position the slot follower 21 reaches the upper end of slot 19.

Handle member 18 operates in a like manner. Thus, pivoting of the rearward leg portion 18c of the handle 18 by means of grip or finger hole 18d about pivot point 18a causes the corresponding pivoting of the forward depending leg portion 18b and its corresponding slot follower 22 extending therefrom, which can then move within slot 20 in the same manner as discussed above with respect to follower 21 and slot 19. Thus, as slot follower 22 is located above pivot point 18a, pivoting of handle member 18 in an upward direction from the position shown in FIGS. 1 or 4 to that shown in FIG. 3 also includes a forward component to urge the slide member 10 forwardly towards the jaw members 3 and 4, again facilitating the closure of the jaws in the manner discussed above.

Figure 2:
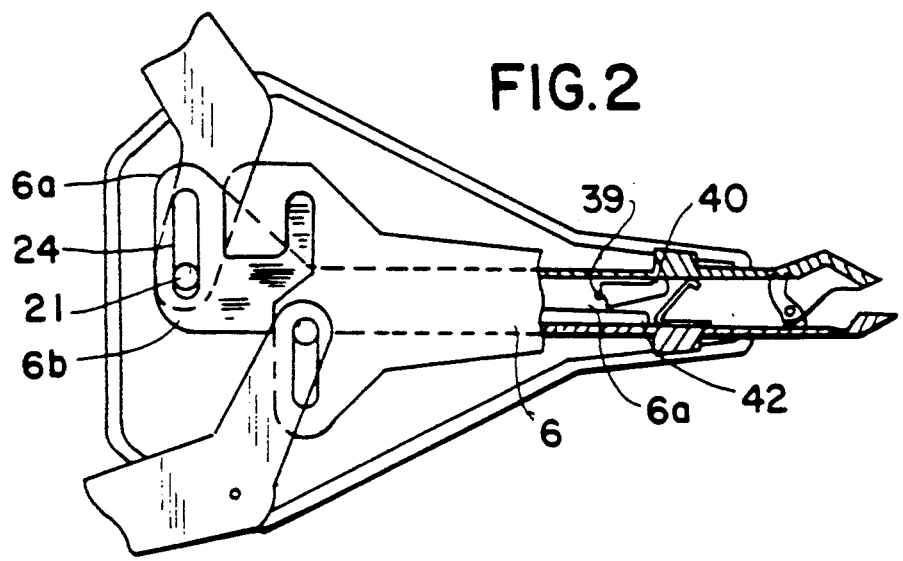
FIG. 2 is a top, plan, partial view of a portion of the apparatus shown in FIG. 1, showing the front end thereof in partial cross-section.
Figure 5:
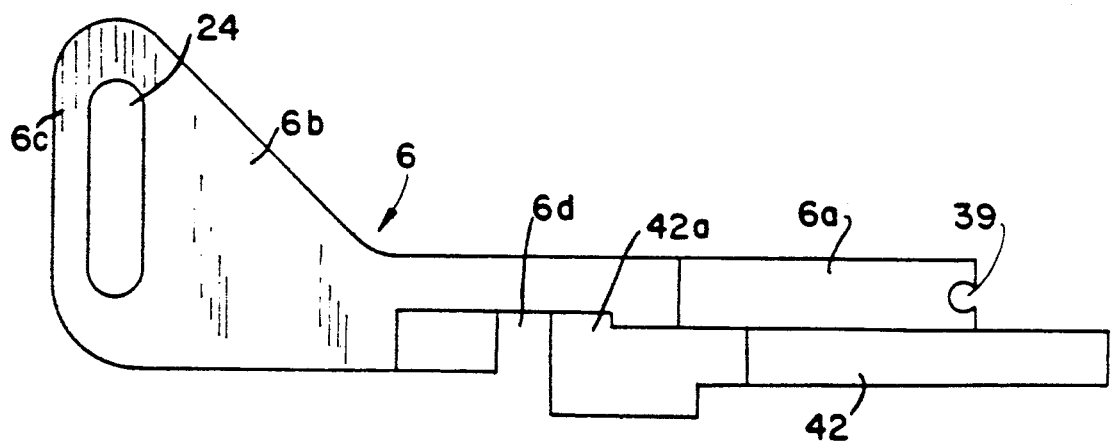
FIG. 5 is a top, plan view of the clip moving component of the apparatus shown in FIG. 1.
Figure 6:
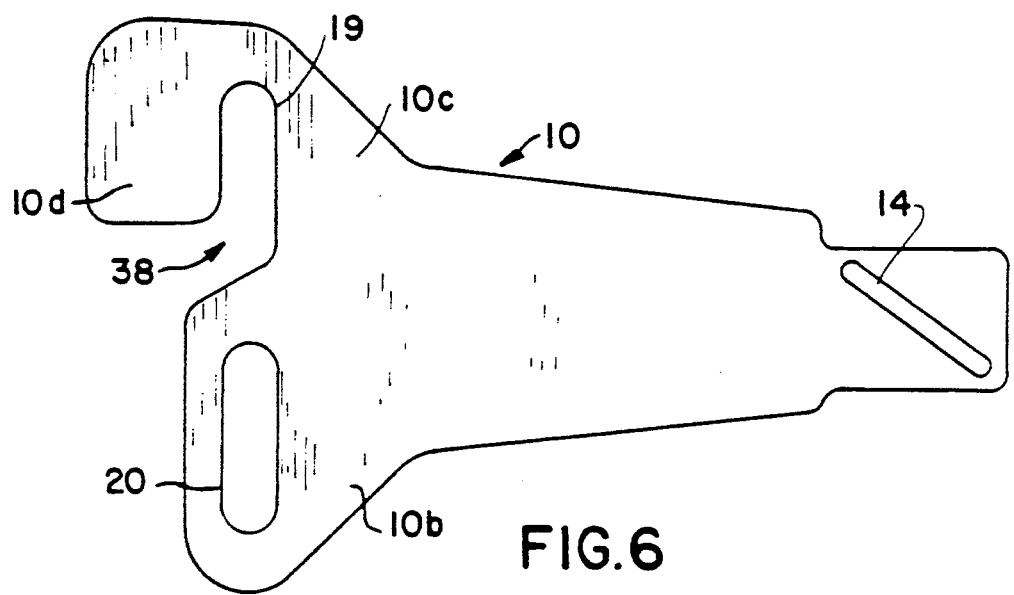
FIG. 6 is a top, plan view of the upper jaw actuating component of the apparatus shown in FIG. 1.

Longitudinally and slidably contained within the housing 2 is clip moving means 6, which is shown apart from the apparatus of the present invention in FIG. 5 and operatively assembled therewith in FIGS. 1 and 2. This elongated element 6 includes a forward end 6a which preferably includes an aperture 39 with a reduced opening into which can be fit the corresponding enlarged circular extension 40a of a pusher member 40 so that the pusher member 40 extends therefrom in the manner shown in FIGS. 2 and 9-13. In addition, a secondary pusher member 42 is slidably juxtaposed below clip moving means 6 by means of shoulder 42a being disposed in recess 6d so that its forward end extends forwardly in the manner shown in FIGS. 2 and 5, where it is below pusher member 40. The rearward end 6b of the clip moving means 6 includes an upstanding leg portion 6c which includes a transverse groove 24 extending therethrough. The clip moving means 6 is slidable between the retracted position shown in FIG. 2 and a forward position in which the groove 24 is in alignment with transverse slot 19 of slide 10. When the clip moving means 6 is in this position the pusher member 40 extends into the clip retaining cavity 5 in a manner discussed below in particular detail with respect to FIGS. 9-13.

Upon opening movement of handle 17 it can be seen that the slide follower 21 extending from the leg portion 17b of handle member 17 can continue to rotate in a clockwise direction in the configuration shown in FIG. 4 and thus exit the transverse slot 19 through aperture 38. Since the slide follower 21 is still projecting into the groove 24 of clip moving means 6, its continued clockwise motion from the position in FIG. 4 to that in FIG. 1 causes the slide member 10 to slide longitudinally from the advanced position thereof to the retracted position, which can be clearly seen in FIG. 2. Thus, the same handle member 17 can be used to manipulate both the slide member 10 and clip moving means 6 depending upon the degree of rotation thereof about pivot point 17a. The capability to control both the movement of the clip moving means 6 with respect to the clip retaining cavity 5, and the opening and closing of jaw members 3 and 4, by the use of handle members 17 and 18 provides a simple and efficient method by which the overall function of the present apparatus can be easily accomplished by a surgeon.

Referring now to FIGS. 7-13, the actual procedure for implanting locking clips to effect percutaneous occlusion of the vas deferens utilizing the embodiment of the present invention as shown in FIGS. 1-6 and 14-16 will now be described.

Figure 13:
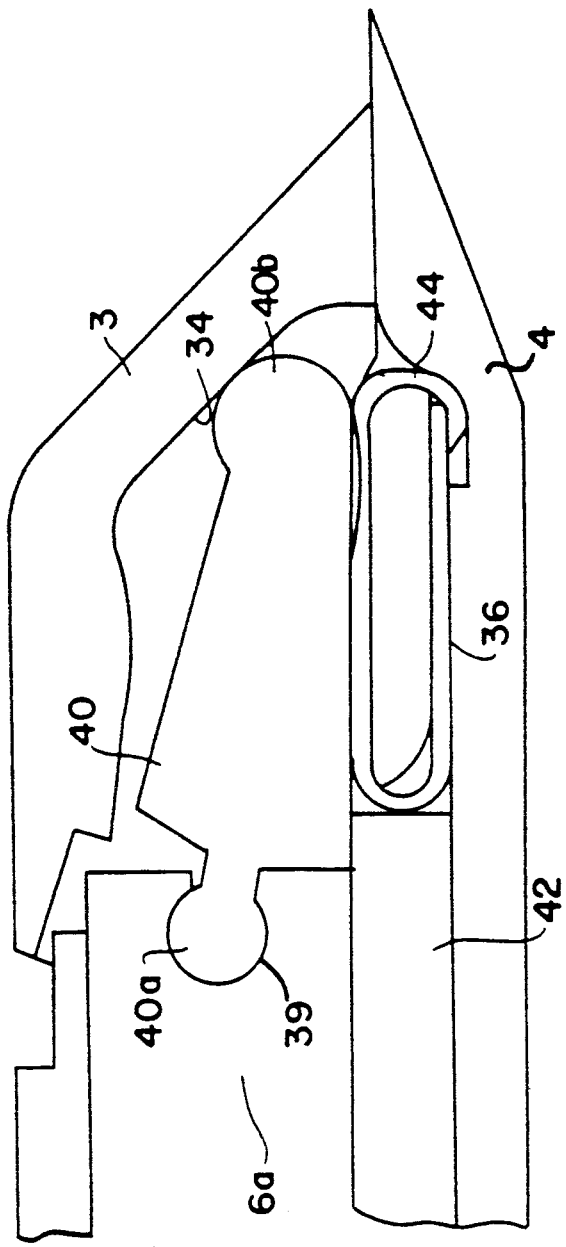
FIG. 13 is a top, plan, enlarged view of the upper and lower jaws of the apparatus shown in FIG. 1 with the jaws closed and the locking clip closed therein.
Figure 14:
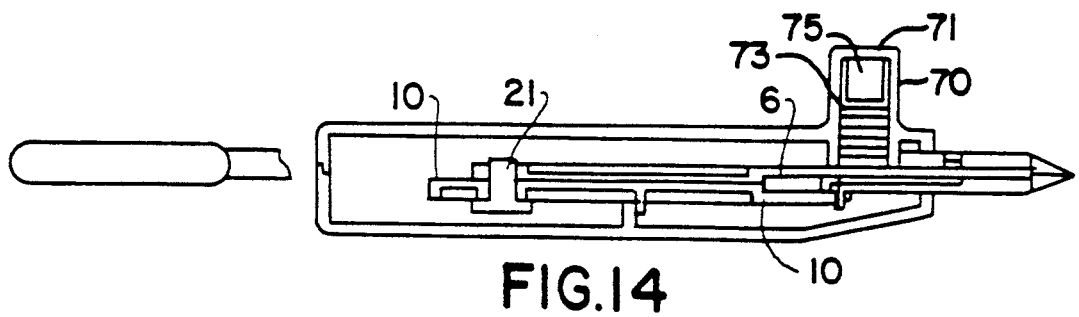
FIG. 14 is a side, elevational, partial view of the apparatus shown in FIG. 1, illustrating in particular the positioning and configuration of the respective sliding members and the clip delivering cartridge.
Figure 15:
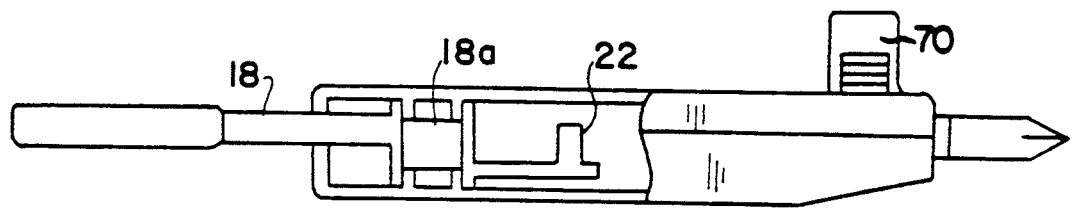
FIG. 15 is a side, elevational, partial view of the apparatus in FIG. 1, illustrating in particular the arrangement of handle 18.

In the entry position shown in FIG. 7, in which the handle members 17 and 18 are in the configuration shown in FIG. 3, the device is introduced by piercing the skin, again by simply moving the device forward while grasping the handles 17 and 18. It should also be appreciated that at this point there is no clip within the clip retaining cavity 5. The clip itself, a sample of which can be seen in FIGS. 9-13 where it is generally designated as 44, is maintained in cartridge 70 which holds a number of clips in alignment therein, as shown in FIGS. 14 and 15.

Cartridge 70, extending outwardly from housing portion 2a, has a spring 75 which exerts a force between end caps 71 and clip pusher 73, thereby constantly urging the clips 44 toward clip moving means 6. When the clip moving means 6 is moved to the retracted position shown in FIG. 2, the proximate clip 44 in cartridge 70 will advance transversely into position in front of pusher 40 and secondary pusher 42 of slide 6, whereby the clip 44 can be moved in a forward direction toward the clip retaining cavity 5 by the rotation of handle member 17, as discussed further below. The remainder of the clips in cartridge 70 are similarly urged transversely so as to be in position for subsequent clamping operations.

As the device is moved further, the trocar obturator configuration 7, with barb 9, continues to move forward towards the vas deferens of the urogenital system. As the vas deferens is approached, the surgeon begins to pivot the upper jaw 3 into an open position by spreading the handle members 17 and 18 from the position shown in FIG. 3 to that shown in FIG. 4. Again, this causes the forward ends 17b and 18b to rotate towards each other, thereby causing the extending slot followers 21 and 22 to rotate within their respective slots 19 and 20, thereby urging the slide member 10 away from the clip retaining cavity 5. This action simultaneously causes the inner end 3a of the upper jaw 3 to rotate downwardly or in a counterclockwise direction as the slot follower 16 thereof travels downwardly in slot 14, thereby opening the jaw into the position shown in FIG. 4.

The surgeon then locates the vas deferens 60 between the jaws in the manner shown in FIG. 8 immediately after piercing the surrounding tissue to expose the same. The surgeon can now remove the device slightly in a rearward direction to again expose the vas deferens 60. With the jaws in the open position, and the clip 44 in its retracted position, the surgeon can now proceed to move the clip into its position within the clip retaining cavity 5, as shown in FIGS. 9 and 10. This is easily accomplished by first retracting the clip moving means 6 (by continuing to rotate handle member 17 in a clockwise direction into the position shown in FIG. 1) whereby the clip 44, in its retracted position will have moved from clip cartridge 70 into the position shown in FIG. 2. By next rotating the handle member 17 in a counterclockwise direction, whereby the slot follower 21 within slot 24 similarly moves in a clockwise direction to urge the clip moving means 6 in a forward direction towards the clip retaining cavity 5, the pusher member 40 in conjunction with the secondary pusher 42 moves the clip 44 towards the clip retaining cavity 5, again as shown in FIG. 9. Because of the location and configuration of pusher member 40 at the upper end of the clip 44, pressure is maintained on the upper end of the clip as it moves forward. In any event, continued motion of the handle member 17 in a counterclockwise direction as discussed above continues to urge the clip towards the clip retaining cavity 5 until it reaches the same as shown in FIG. 10.

At this point, the vas deferens 60 is contained within cavity 5 and clip 44. Thus, continued motion of the clip moving means 6 in the forward direction will cause the clip 44 to begin closing as shown in FIGS. 11-13, initially by means of the pusher member 40 and secondary pusher member 42 so as to urge the upper end of the clip 44 against the camming surface 34. As the clip moving means 6 continues to move forward, the clip 44 begins to close against the camming surface 34, as is particularly illustrated in FIGS. 11 and 12. At the same time, further closure and final closing of the clip 44 into the configuration shown in FIG. 13 is ultimately caused by a combination of continued movement of the pusher member 40, whereby its boss member 40b bears against the camming surface 34 and additional closure of the jaw members 3 and 4, such continued movement being facilitated by pivoting of handle members 17 and 18 into the closed configuration shown in FIG. 3. More specifically, after rotation in a counterclockwise direction of handle 17 is completed to the extent that the slot follower 21 enters the slot 19, continued closure of the handle members 17 and 18, i.e., so that the handle members approach each other, now closes the jaw members 3 and 4, thus resulting in complete closure of the clip around the vas deferens as shown in FIG. 13. It should be noted that the closing and locking of clip 44 is further facilitated by means of recess 4a and camming surface 4b of jaw member 4, both of which features are shown in FIGS. 9-13. As the foot 44a at the upper end of clip 44 is urged toward jaw member 4, surface 44b at the tip thereof will first bear against camming surface 4b. Further movements of clip 44 by means of pusher member 40 will cause the foot 44a of clip 44 to turn inwardly as surface 44b bears against surface 4b. Continued movement of pusher member 40 will urge foot 44a into recess 4a where the same will be folded about end 44c of clip 44, thereby locking the clip 44 around the vas deferens.

The occlusion of the vas deferens is now complete, preventing the passage of sperm from the testes to the ejaculatory duct. Removal of the device from the vas deferens 60 is now accomplished by opening the jaw members 3 and 4 and merely removing the device therefrom.

Thus, the present invention accomplishes occlusion of the vas deferens in a rapid and efficient manner. Typically under about 5 minutes, with minimum invasion of the body, is required.

Figure 28:
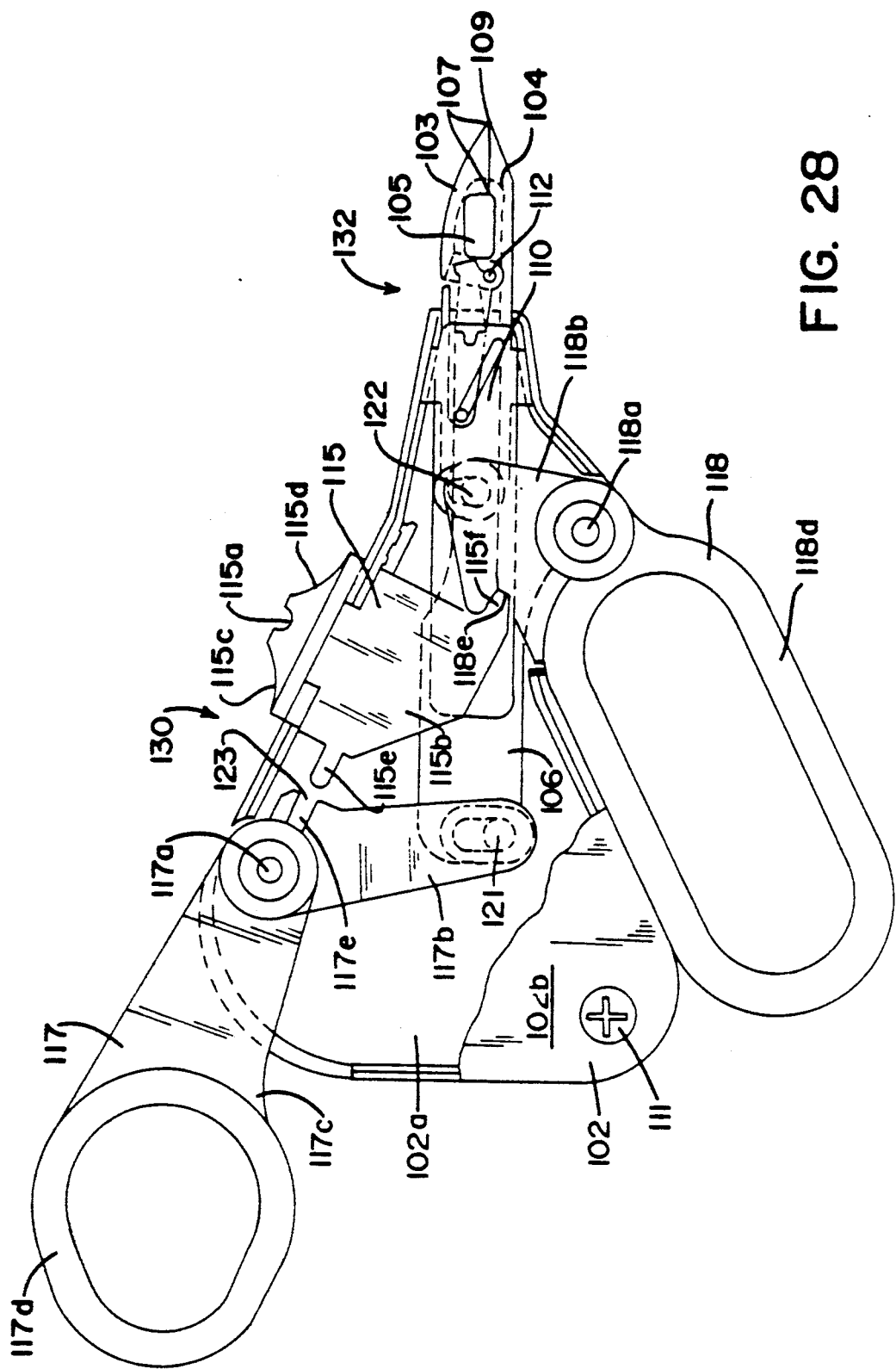
FIG. 28 is a top, plan view of a preferred embodiment of the apparatus in accordance with the present invention, with the top cover partially broken away to illustrate in particular the inner workings thereof, and showing the selector switch in position to advance and close a locking clip about the vas deferens.
Figure 29:
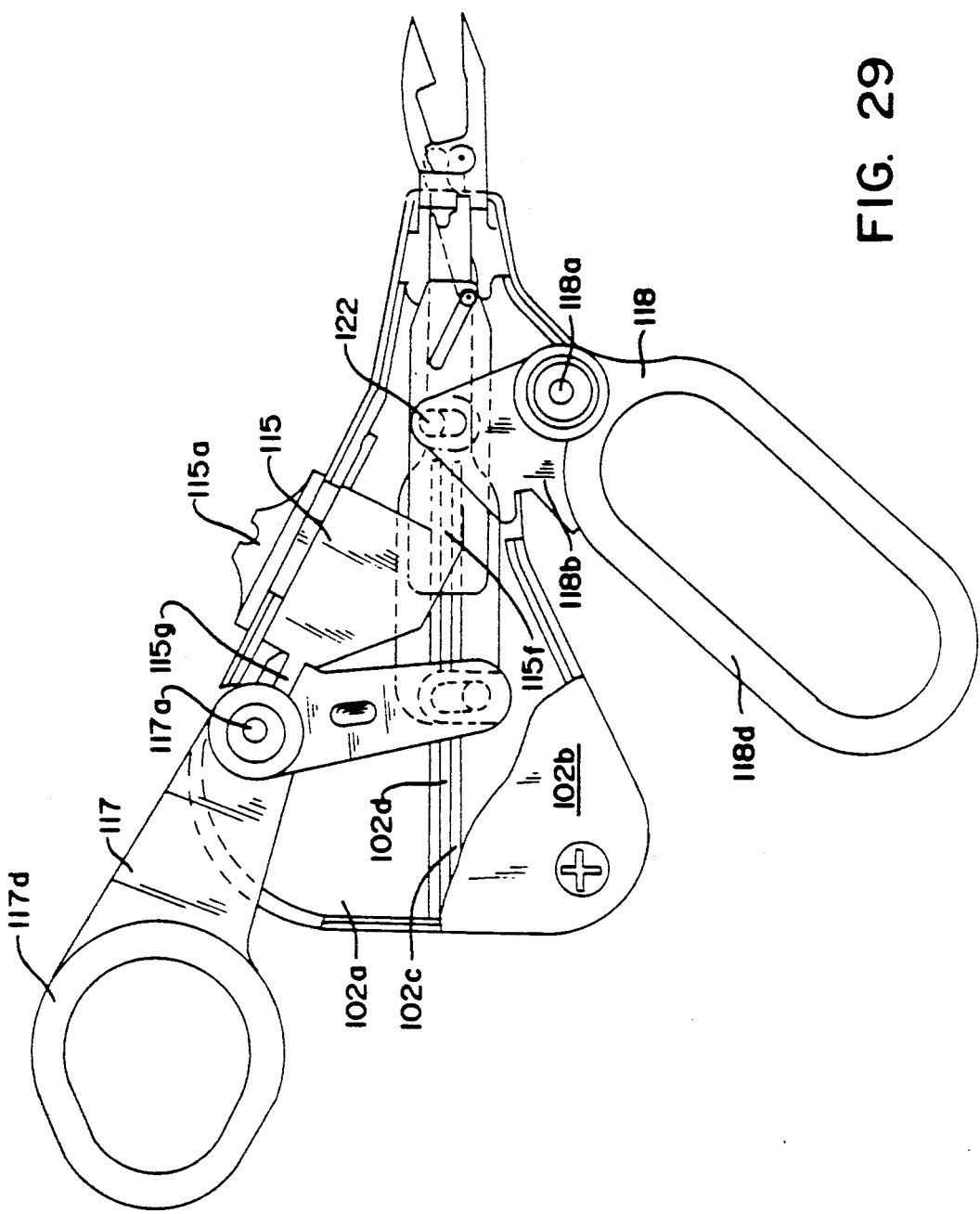
FIG. 29 is a top, plan view of the apparatus shown in FIG. 28, showing the selector switch in position for opening or closing the jaw members.

A highly preferred embodiment of the apparatus of the present invention is shown in FIGS. 28-38. As can be seen in FIG. 28, the overall apparatus 100 includes a body portion 130, a pair of handles 117 and 118, a selector switch 115, and a front end 132 comprising a pair of jaws 103 and 104 terminating in a trocar obturator configuration 107.

The body portion 130 includes two housing members 102a and 102b which can be assembled by threaded means, as at 111, or any other suitable means. In assembled position, housing members 102a and 102b include openings for the handle members 117 and 118, the front end 132 and the selector switch 115. The trocar obturator 107 operates in the same manner as the trocar obturator 7 of the previously described embodiments. Thus, sharply pointed end 109 penetrates and cuts through tissue so that trocar obturator 107 may trap a target vessel and implant a clip thereon.

As can be seen in FIG. 28, the jaw members 103 and 104 of the preferred embodiment of the present invention are pivotably connected at pivot point 112. Upper jaw member 103, shown in detail in FIGS. 35-38, is cup-shaped in form, and includes an inner wall surface comprising a forward camming surface 134. The lower jaw 104, shown in detail in FIGS. 32-34, includes a substantially flat upper surface 136. Upper jaw 103 and lower jaw 104 thus define a clip retaining cavity 105 therebetween.

Jaw members 103 and 104 are associated and operated in a manner substantially similar to that described above with regard to the apparatus of FIG. 1. Thus, lower jaw 104 includes a rearwardly extending portion 137 having outwardly extending tabs 137a on either side which act to substantially fix the position of the lower jaw with respect to the housing portion 102b. By utilizing slide 110, slidably disposed within the housing 102, to pivot the upper jaw 103 about pivot point 112, the jaws can be opened and closed. The forward end 110a of the slide 110 adjacent to the jaw members 103 and 104 includes an angularly disposed track 114 extending therethrough. A track follower 116, extending from the rear portion 103a of the upper jaw 103 into the track 114, follows track 114 as slide 110 is moved from a distal position remote from the clip retaining cavity 105 to a proximate position adjacent to the clip retaining cavity 105, and thereby raises rear portion 103a of the upper jaw 103 so that the forward end 103b of the upper jaw 103 closes toward the fixed lower jaw 104. Thus, when the slide 110 is in the proximate position shown in FIG. 28 the jaws 103 and 104 are in a fully closed position.

Figure 31:
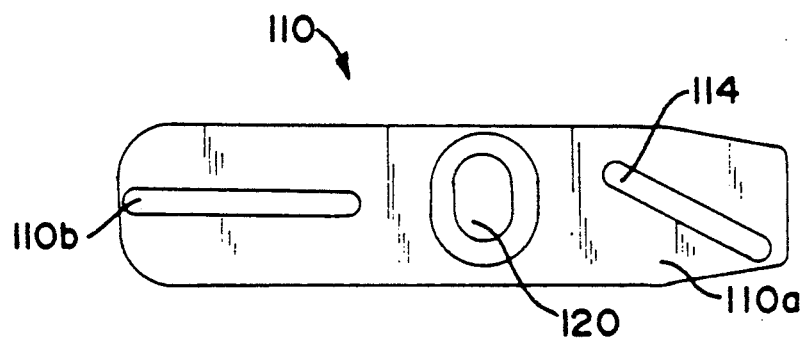
FIG. 31 is a top, plan view of the upper jaw actuating component of the apparatus shown in FIG. 28.
Figure 32:
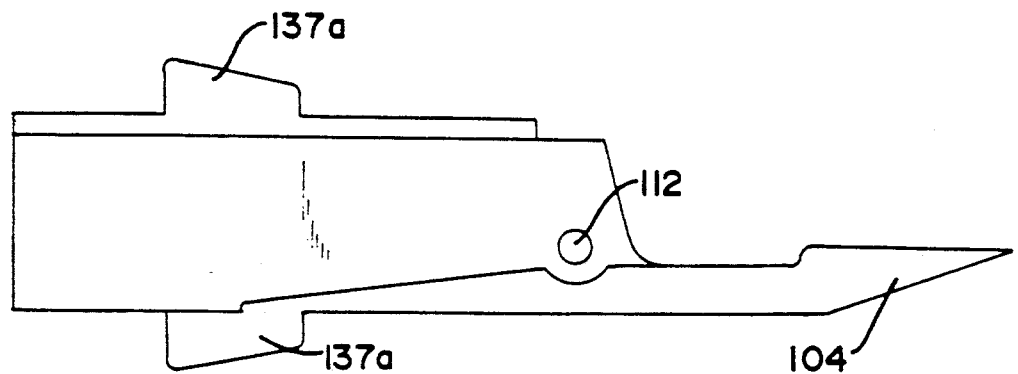
FIG. 32 is a top, plan view of the lower jaw of the apparatus shown in FIG. 28.
Figure 33:
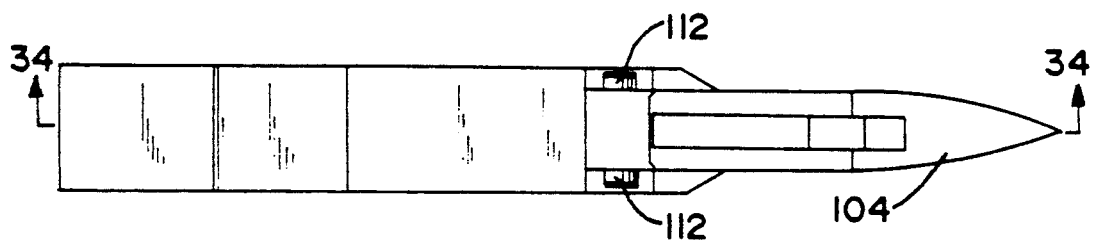
FIG. 33 is a side, elevational view of the lower jaw shown in FIG. 32.
Figure 34:
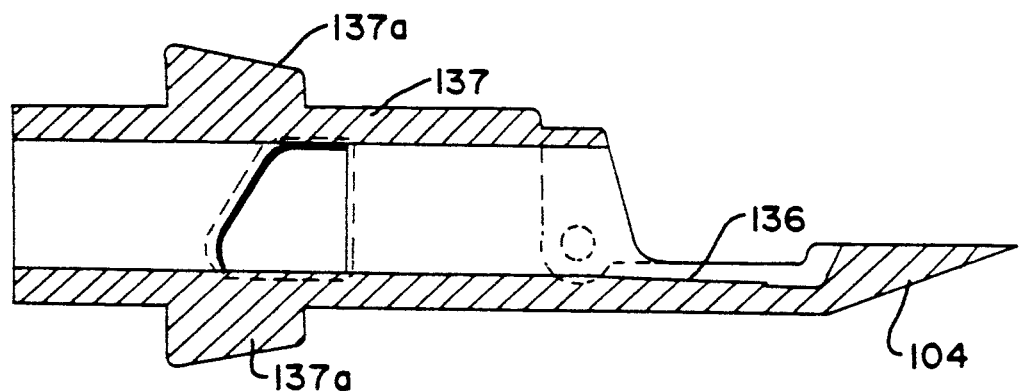
FIG. 34 is a cross-sectional view of the lower jaw taken on line 34—34 of FIG. 33.
Figure 35:
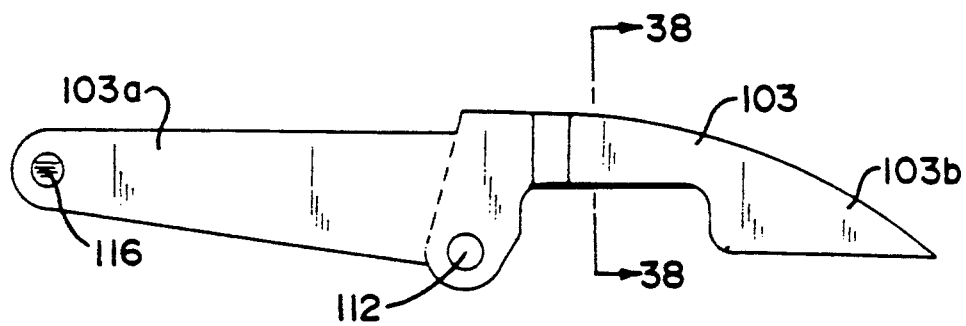
FIG. 35 is a top, plan view of the upper jaw of the apparatus shown in FIG. 28.
Figure 36:
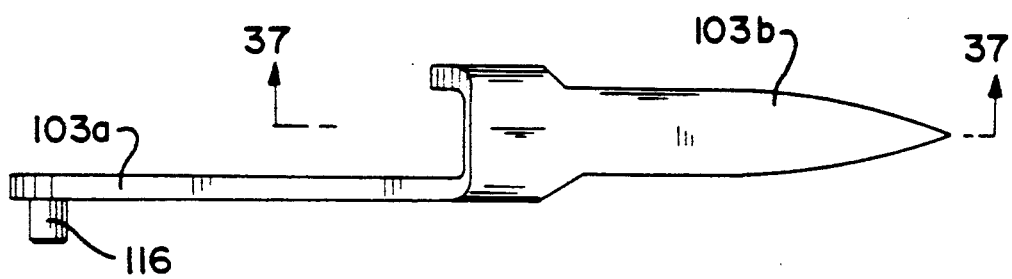
FIG. 36 is a side, elevational view of the upper jaw shown in FIG. 35.
Figure 37:
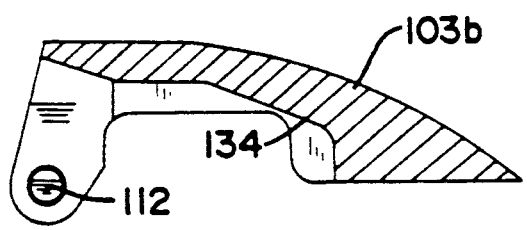
FIG. 37 is a cross-sectional view of the upper jaw taken on line 37—37 of FIG. 36.
Figure 38:
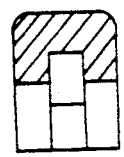
FIG. 38 is a cross-sectional view of the upper jaw taken on line 38—38 of FIG. 35.

The movement of slide 110 within the housing 102 is effectuated by the action of handle 118. As shown in FIG. 31, the central portion of slide 110 includes transverse slot 120. Handle 118, privotally connected between housing members 102a and 102b at pivot point 118a, includes a forward portion 118b and a rearwardly projecting grip or finger hole 118d. Rotation of the grip 118d about pivot point 118a will thus result in a corresponding displacement of the forward portion 118b of the handle 118. Disposed at the forward portion 118b of the handle 118 is a projecting slot follower 122 extending into the slot 120 of the slide 110. Since the slow follower 122 is located above the pivot point 118a, the motion of the slot follower 122 includes a forward longitudinal component directed toward the jaws 103 and 104. This, in turn, causes the slide 110 to move forwardly into the position shown in FIG. 28, at which position the slot follower 122 reaches the lower end of the slot 120.

Figure 30:
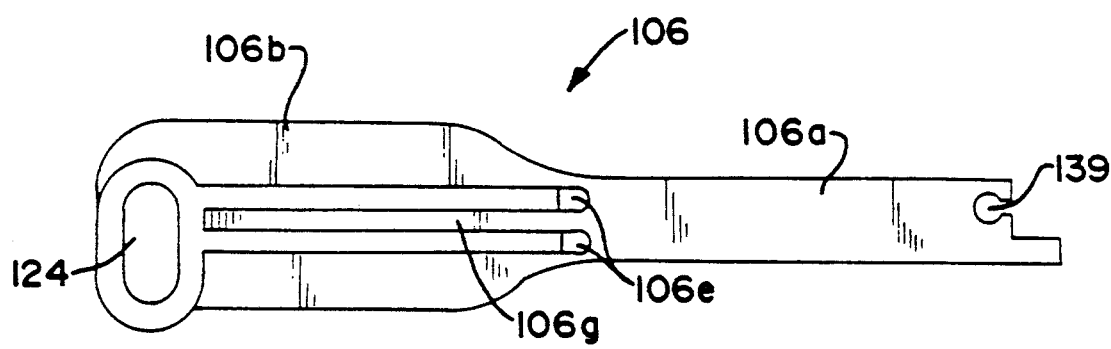
FIG. 30 is a top, plan view of the clip moving component of the apparatus shown in FIG. 28.

Longitudinally and slidably contained within the housing 102 is clip moving means 106, shown separately in FIG. 30. A forward end 106a of clip moving means 106 includes an aperture 139 with a reduced opening, sized and shaped for mating engagement with the enlarged circular extension 140a of a pusher member 140 in the manner described in the previous embodiment and as shown in FIGS. 9-13 thereof. The rearward end 106b of the clip moving means 106 includes a transverse groove 124 extending therethrough. The clip moving means 106 is slidable between a retracted position remote from the clip retaining cavity 105 and a forward position proximate to the clip retaining cavity 105. When the clip moving means 106 is in the forward position the pusher member 140 extends into the clip retaining cavity 105 in a manner discussed more particularly below.

Longitudinally disposed ribs on the slide 110 and the clip moving means 106 keep these members properly aligned and spaced with respect to one another and to the housing 102. Thus, ribs 110b and 110c are longitudinally disposed on either side of the slide 110, and ribs 106e and 106f are longitudinally disposed on either side of the clip moving means 106, ribs 106e defining channel 106g therebetween. In assembled position, rib 110b engages housing member 102a and rib 110c matingly engages and is guided by channel 106g. Rib 106f, in turn, matingly engages and is guided by channel 102d formed between longitudinally disposed ribs 102c on housing member 102a. This association enables the reciprocating movement of the slide 110 and the clip moving means 106 within the housing 102 so that the apparatus of the present invention may properly function without jamming or binding.

The movement of the clip movement means 106 between the forward position and the retracted position is effected by the action of handle 117. Handle 117, pivotally connected between housing portions 102a and 102b about pivot point 117a, includes a forward depending leg portion 117b angularly disposed with respect to rearward leg portion 117c which terminates in grip or finger hole 117d. Disposed at the forward portion 117b of the handle 117 is a projecting slot follower 121 extending into slot 124. Thus, rotation of the handle 117 in a counterclockwise direction causes a corresponding displacement of the forward portion 117b thereof, so that the slot follower 121 moves upwardly within slot 124. However, since the slot follower 121 is located below pivot point 117a, the motion of the slot follower 121 includes a forward longitudinal component directed towards the jaws 103 and 104, which causes the clip moving means 106 to move forwardly into the clip retaining cavity 105.

Slidably mounted between housing members 102a and 102b is a selector switch 115. Top portion 115a of selector switch 115 extends outwardly from an opening formed in the side of the housing and includes oppositely disposed curved surfaces 115c and 115d for forward and rearward activation of the switch 115. The bottom portion 115b of the switch 115 includes a forwardly extending hook 115f which, when the selector switch is in forward position, matingly engages a recess 118e formed in the forward portion 118b of handle 118. The hook 115f can only mate with the recess 118e when the handle 118, and thus the jaw, is in a fully closed position. Thus, jaw members 103 and 104 can be locked in the closed position by the movement of selector switch 115 into the forward position.

Projecting rearwardly from the bottom portion 115b of selector switch 115 is a tab member 115e which, when the selector switch 115 is in a rearward position, matingly engages slot 117e formed on the lower portion 117b of handle 117 adjacent to pivot point 117a. Slot 117e, however, is not fully enclosed, and includes an aperture 123 extending forwardly therefrom. By sliding selector switch 115 in a rearward direction, tab 115e can enter aperture 123 and mate with slot 117e. Handle 117 can only be locked in place by this action when in the fully closed position, with clip moving means 106 extended fully forward into clip retaining cavity 105. The rearward positioning of selector switch 115 removes the hook 115f from the recess 118e in the forward portion 118b of the handle 118 so that the jaw members 103 and 104 may be opened. Similarly, the forward positioning of the selector switch 115 removes the tab 115e from the slot 117e in the bottom portion 117b of the handle 117 so that the clip moving means 106 may be retracted from or advanced toward the clip retaining cavity 105. Thus, as only one of handles 117 and 118 can be operated at a time, the preferred embodiment is simpler and less awkward to use than the embodiment previously described above.

As the preferred embodiment of the present invention operates in a manner substantially similar to the embodiment previously described, reference can be made to FIGS. 7-13 thereof in describing the actual procedure for implanting locking clips to effect percutaneous occlusion of vas deferens. That is, although there are differences in operation of these overall devices, the resultant action of the respective front ends 32 and 132 thereof are substantially identical.

In the entry position shown in FIG. 7, the handles 117 and 118 are in the closed configuration and the selector switch 115 is in the forward position, thereby locking jaws 103 and 104 closed, all of which can readily be seen in FIG. 28. Additionally, there is no clip present within the clip retaining cavity 105. The clip, generally designated as 44, is the same as that used in the previous embodiment discussed above. Cartridge 70, similar to that shown in FIG. 14 and 15, maintains a number of clips in alignment therein, feeding them one at a time to the clip moving means 106 as discussed above.

As the device is moved forward, the pointed tip 109 of the trocar obturator configuration 107 pierces the skin and moves toward the vas deferens of the urogenital system. As the vas deferens is approached, the surgeon slides selector switch 115 rearwardly so that handle 118 can be downwardly rotated. This causes the forward end 118b to rotate in a counterclockwise direction which urges the slide 110 away from jaws 103 and 104. Inner end 103a of the upper jaw 103 is simultaneously rotated downwardly or in a counterclockwise direction as the slot follower 116 thereof travels downwardly in slot 114, thereby opening the jaw to the position shown in FIG. 29.

As shown in FIG. 8, the surgeon pierces the surrounding tissue to expose the vas deferens 60 and locates the same between the jaws 103 and 104. Once the vas deferens 60 is so located, handle 118 is rotated in a clockwise direction which urges slide 110 forwardly. This, in turn, causes the inner end 103a of the upper jaw 103 to rotate upwardly or in a clockwise direction as the slot follower 16 thereof travels upwardly in slot 114, thereby closing jaw members 103 and 104 into the position shown in FIG. 28. When the jaws 103 and 104 have obtained a fully closed position, they can be locked therein by moving selector switch 115 to a forward position, thereby engaging hook 115f in recess 118e as previously described. Since hook 115f will only become aligned with recess 118e when the jaws 103 and 104 are fully closed, the ability or inability to slide the selector switch to the forward position serves to indicate to the surgeon the position of jaw members 103 and 104 with respect to one another.

At this point, with the selector switch 115 in a forward position, handle 117 may be freely rotated to move the clip 44 into its position within the clip retaining cavity 105, as can be understood by reference to FIGS. 9-13. It should be emphasized at this point that the reference to FIGS. 9-13 in the following description of the movement of the clip 44 into its position within the clip retaining cavity 105 in accordance with the preferred embodiment of the present invention is made solely to illustrate the position of the pusher member 140 and the clip 44 relative to the clip retaining cavity 105, and that jaw members 103 and 104 remain locked in a closed position as described above. Thus, by rotating handle 117 in a clockwise direction the clip moving means 106 is retracted so that the clip 44 can move from the clip cartridge 70 into the position shown in FIG. 9. By next rotating the handle 117 downward, the slot follower 121 within slot 124 is caused to move in a counterclockwise direction, thereby urging the clip moving means 106 in a forward direction towards the clip retaining cavity 105. Simultaneously, the pusher member 140 moves the clip 44 towards the clip retaining cavity 105. The continued rotation of the handle 117 in a counterclockwise direction continues to urge the clip 44 towards the clip retaining cavity 105, as discussed above, until it reaches the same wherein the vas deferens 60 is contained within cavity 105 and clip 44, as shown in FIG. 10. The continued motion of the clip moving means 106 in the forward direction will cause the clip 44 to close around the vas deferens 60, in a manner similar to that set forth above with regard to the previously described embodiment. Thus, the forward movement of the pusher member 140 urges the upper end of the clip 44 against the camming surface 134. As the clip moving means 106 continues to move forward, the clip 44 begins to close against the camming surface 134, as can be seen in FIGS. 11-13. Further closure of the clip 44 is caused by the continued movement of the pusher member 140, whereby its boss member 140b bears against the camming surface 134, thus resulting in complete closure of the clip 44 around the vas deferens 60 as shown in FIG. 13. The surgeon can then slide selector switch 115 in a rearward direction so that tab 115g can matingly engage slot 117e, as noted above. In this position, handle 117 will be locked from further movement, and clip moving means 106 will be similarly locked in a forward position. As selector switch 115 can only be moved rearwardly when tab 115g is aligned with aperture 123 in slot 117e, the ability of the surgeon to move the switch in this direction will serve to indicate that the clip moving means 106 has been fully extended in a forward direction, and that clip 44 has been completely closed and locked around the vas deferens 60. As noted with regard to the previously described embodiment, the closing and locking of clip 44 is aided by means of recess 104a and camming surface 104b of lower jaw member 104, the details of which can be seen in FIGS. 9-13. As clip 44 closes, the foot 44a at the upper end thereof is urged toward lower jaw member 104, until surface 44b at the tip of foot 44a first bears against camming surface 104b. The continued closure of clip 44 by means of pusher member 140 will cause the foot 44a of clip 44 to turn inwardly as surface 44b bears against camming surface 104b. As closure proceeds, foot 44a will be urged into recess 104a where the same will be folded about end 44c of clip 44, so that the clip 44 becomes locked around the vas deferens as above.

As the selector switch 115 is engaged in the rearward position, removal of the device from the vas deferens 60 can be readily accomplished by rotating handle 118 in a counterclockwise direction, thereby opening the jaw members 103 and 104 and removing the device therefrom.

Another embodiment of the apparatus of the present invention is shown in FIGS. 24-27. In this embodiment a pair of jaw members 45 and 46 are interconnected by relative pivotable movement toward and away from each other. These jaw members 45 and 46 are adapted to hold an open clip 47 in operable position to enclose a target vessel 42. Clip 47 has a triangular configuration in this case, which is slightly different from the clips discussed above. Clip 47 is located between an upper fixed jaw member 45 and a lower pivotable jaw member 46 in the device shown therein. This lower jaw member 46 retains the bottom portion of clip 47 while the upper portion of the clip is held in operable position by the upper jaw member 45. The clip is inserted as part of a pivoting, scissor-like motion which is effected as ring 48 is moved downwardly. This action causes closure and locking of the clip 47 about the vas deferens 42. As can be seen in FIG. 24, a passage 49 is contained within the jaw member 45, and this passage 49 enables slide member 50 to have a telescoping movement within the lower jaw member 46. Slide member 50 has, at its distal end, a trocar obturator 51 which has a variety of functions including penetration and cutting through tissue and trapping a target vessel substantially similar in operation to those described above in connection with the preferred embodiment of the present invention.

The procedure used for implanting locking clips to effect percutaneous occlusion of the vas deferens with this embodiment of the invention involves insertion of the trocar obturator 51 in a forward direction by use of ring 52. Ring 52, in turn, is attached to the proximal end of the slide member 50 which has at its distal end trocar obturator 51. Thus, by moving the trocar obturator 51 in a forward direction tissue can be cut and the vas deferens exposed in a manner similar to that discussed above. The vas deferens 42 can be entrapped within the open clip 47, and once this occurs the lower jaw member 46 can be moved upwardly as ring 48 is moved downwardly, thereby effecting closure of the clip 47 about the vas deferens 42. Downward movement of the lower jaw member 46 thus leaves clip 47 implanted on the vas deferens as above.

DETAILED DESCRIPTION OF A PREFERRED EMBODIMENT

Another highly preferred embodiment of the apparatus of the present invention is shown in FIG. 40-55. This embodiment has application not only to vasectomies in accordance with the above disclosure, but more generally to various laproscopic procedures where the implantation of a clip is required. It is first noted that the device shown in FIG. 40 does not include a trocar-type obturator at the tip portion thereof. To the contrary, this device includes means which are solely used for the implantation of a clip in a highly efficient manner, but which is not specifically designed to effect the cutting of tissue. Using this apparatus, it is therefore possible to assure correct and appropriate clip implantation during various surgical procedures. The mechanism shown in this device thus secures the targeted vessel or tissue within which the vessel may reside, acting as a hemostat therefor. The area itself, which has been isolated and surgically controlled, is then ligated with precision placement of a clip thereon.

Figures 43, 44, 45:
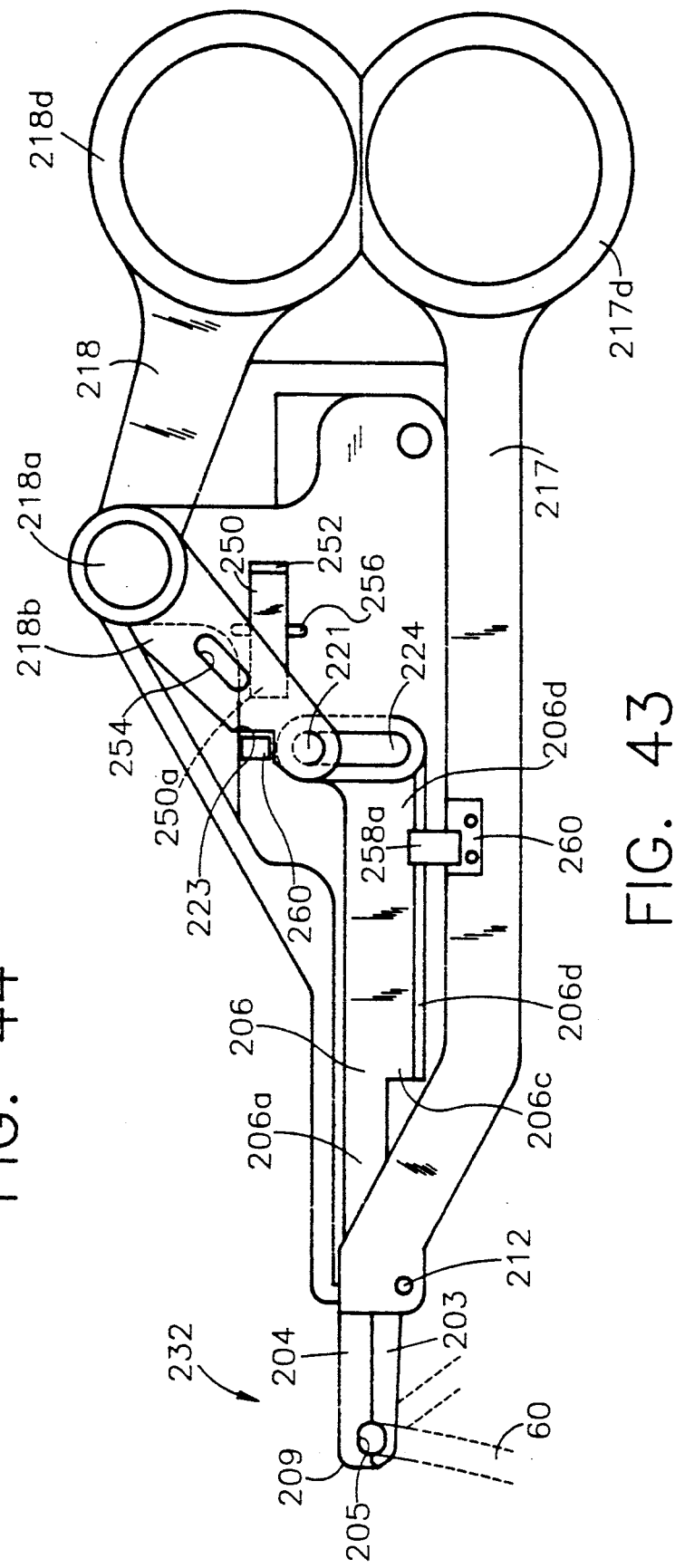
FIG. 43 is a top, elevational view of the device shown in FIG. 40, with the clip advancing and closing mechanism at its forward position.
FIG. 44 is an elevational, perspective view of a clip after application by the device of the present invention.
FIG. 45 is a front, partial view of a variation of the jaws of the device of the present invention.
Figure 46:
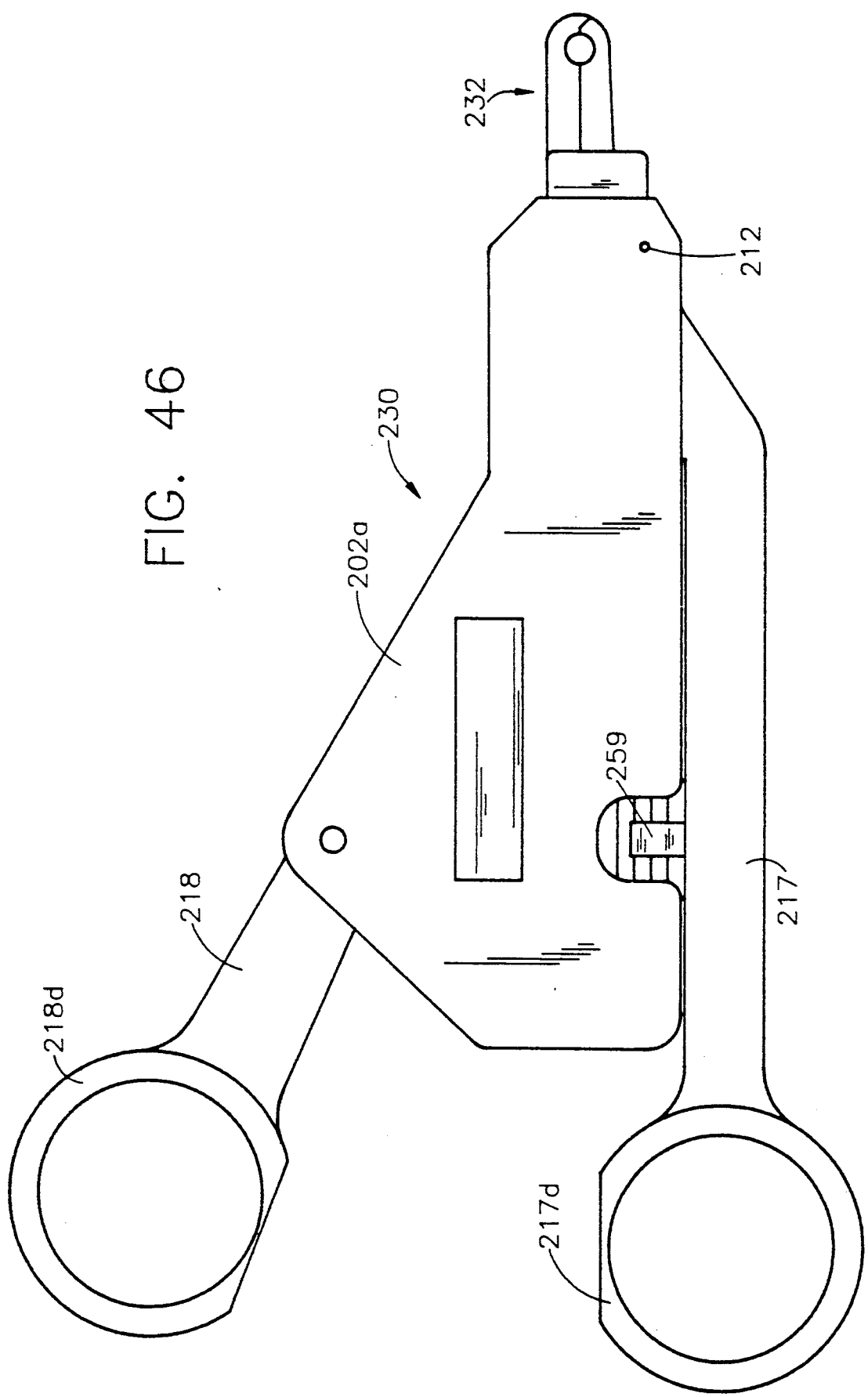
FIG. 46 is a top, elevational view of the device shown in FIG. 40, including the housing therefor.
Figure 47:
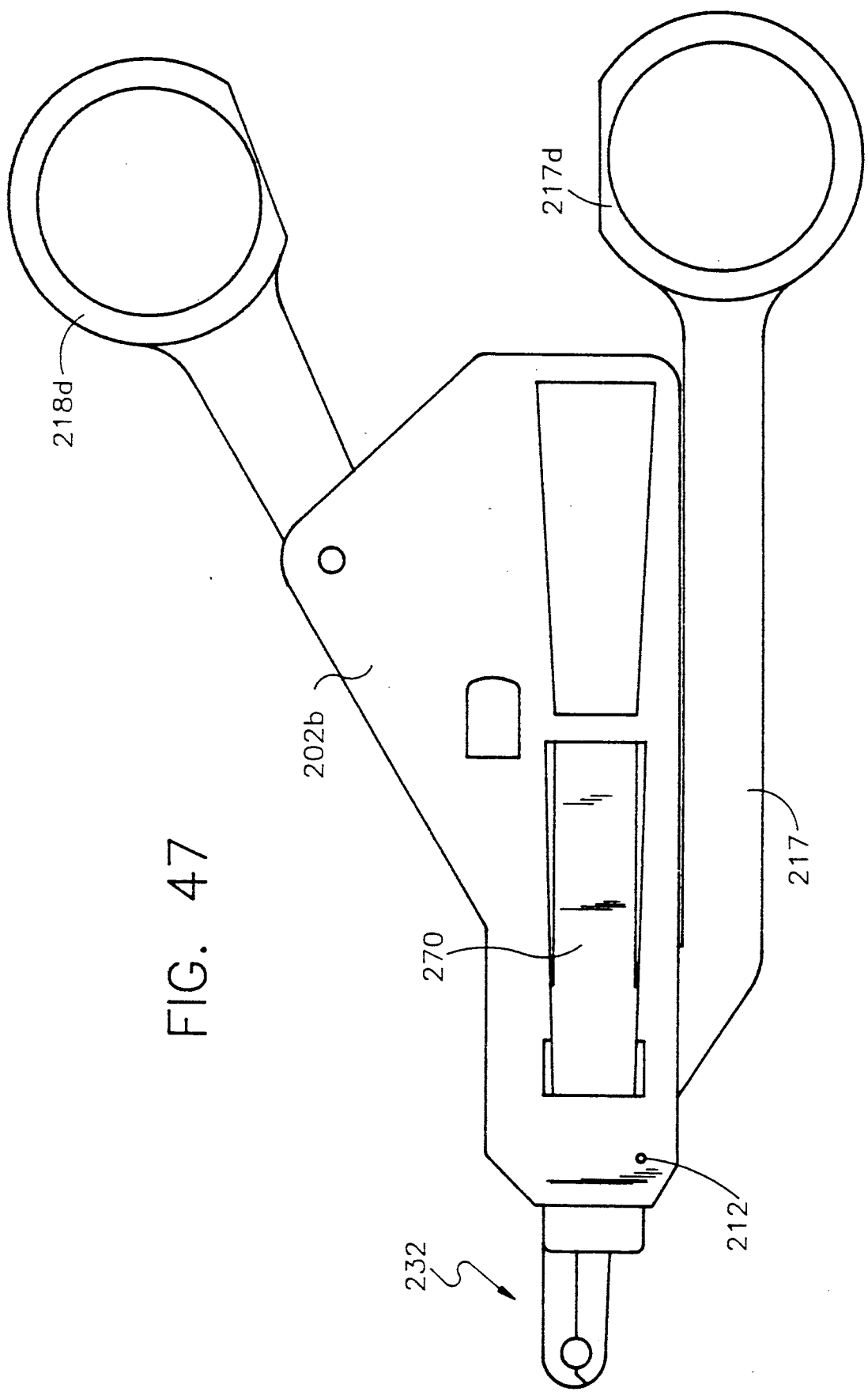
FIG. 47 is a bottom, elevational view of the device shown in FIG. 46.

Turning to the preferred embodiment of the present apparatus shown in FIGS. 40-43, the overall mechanism 200 employed in this apparatus, which is to be disposed between a pair of body portions as is shown in FIGS. 46 and 47, includes a pair of handles 217 and 218, and a front end 232 comprising a pair of jaws 203 and 204. Jaw 204 is an extension of handle 217.

The jaws 203 and 204 themselves terminate in a smooth, rounded end face 209 when closed, as can best be seen in FIGS. 41-43. The end face 209 shown in the device shown in FIGS. 41-43 can thus be contrasted to the trocar-type obturator configuration 107, for example, in the device shown in FIG. 28. In this case, no such mechanism for the cutting of tissue or the like is provided. The sole function of this device is to segregate the target vessel within an opening 205 provided by the inner surfaces of the jaws 203 and 204. The target vessel can thus be maintained entirely within opening 205 when the jaws 203 and 204 are closed, and prior to application of the clip thereto.

In a highly preferred embodiment, the inner surface of opening 205, instead of being circular as shown in FIG. 40, provides an opening 205a as shown in FIG. 45. In this manner, not only can the target vessel be retained within this opening 205a, but it can be compressed to precisely the same degree as will be the case when the clip is applied subsequently thereto. The surgeon can thus pre-test the vessel to check for bleeding and the like, and predetermine whether the clip will be successfully applied thereafter without actually applying the clip, thus preventing unnecessary damage to the vessel, etc.

The body portion 230 of the device shown in FIGS. 40-43 includes two housing members 202a and 202b, the outer surfaces of which can be seen in FIGS. 46 and 47.

These two housing members can be assembled in a similar manner to the members discussed above, such as by use of the threading means discussed in these other embodiments, or any other suitable means. In their assembled condition, housing members 202a and 202b include openings for the handle members 217 and 218, and the front end 232. As can further be seen in FIG. 40, the jaw members 203 and 204 of this preferred embodiment of the present invention include a jaw member 204 which is an extension of handle member 217, and which is pivotably connected at pivot point 212. Jaw member 203, however, is permanently affixed in the position shown in FIG. 40 and does not pivotally or in any other manner alter its position with respect to the housing of the device in question.

Figure 50:
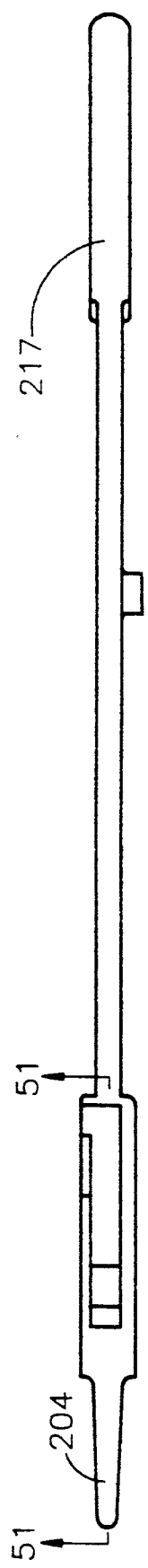
FIG. 50 is a top, elevational view of another handle member used in the device shown in FIG. 40.
Figure 52:
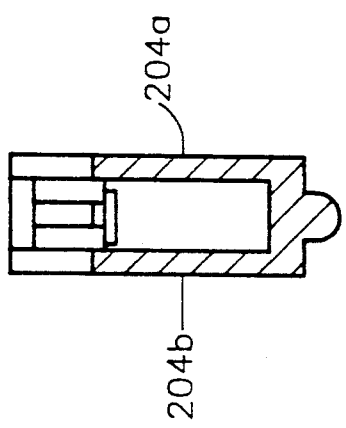
FIG. 52 is a front, partially sectional view of a portion of the handle shown in FIG. 51.
Figure 51:
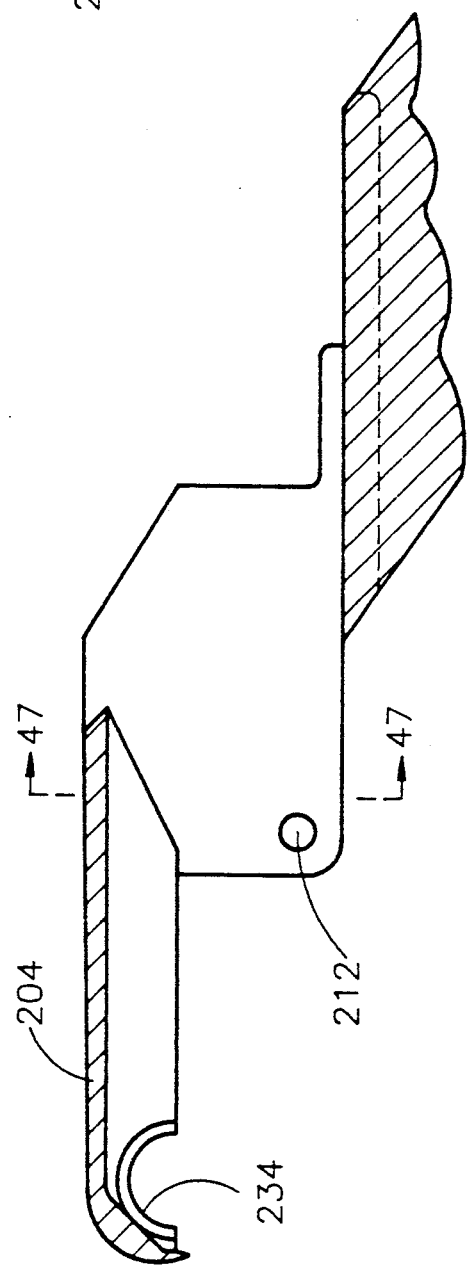
FIG. 51 is a side, partial, partially sectional view of the handle member shown in FIG. 50 taken along lines 51-51 thereof.

Referring specifically to FIGS. 50-52, handle member 217 is shown therein, including its forward end comprising jaw member 204. This jaw member 204 has a U-shaped cross-sectional configuration provided by a pair of side walls 204a and 204b, and the jaw member 204 includes an inner wall surface which preferably includes a camming surface 234. Stationary jaw member 203 also has a U- or cup-shaped cross-sectional configuration, and preferably also includes such a camming surface 234. The two jaw members 203 and 204 thus define a clip retaining cavity therebetween, and the complimentary camming surfaces can effectively assist in closing a clip impelled thereagainst. The opening and closing of jaws 203 and 204 is solely effected by the movement of handle member 217. In particular, clockwise movement of the handle 217d at the end of handle member 217 from the position shown in FIG. 41 to the position shown in FIG. 40 rotates the jaw member 204 upwardly into the phantom position shown in FIG. 40, thus opening the jaws. Similarly, counterclockwise rotation back into the position shown in FIG. 41 closes the jaws into the configuration shown therein. When the jaws are opened to the configuration shown in FIG. 40, a target vessel 60 can be manipulated between the jaws or retained within the clip retaining cavity 205 in the manner shown in phantom view in FIG. 40. It is then possible to close the jaws into the configuration shown in FIG. 41, leaving the target vessel fully retained within the clip retaining cavity 205 without having effected any clip application whatsoever. The surgeon can then be assured that the target vessel has been isolated and retained in position before initiating any such clip applying procedure. Again, in connection with the embodiment shown in FIG. 45, with the opening between the jaws having the configuration shown therein, the surgeon can at the same time determine whether the target vessel will be appropriately occluded by the clip even before it has been applied.

Longitudinally and slidably contained within the housing 202 is clip moving means 206, specifically shown in FIGS. 40-43. A forward end 206a of clip moving means 206 includes pincers 239a and 239b. Thus, in this embodiment pincers 239a and 239b not only perform the function of the previously disclosed pusher member 140 shown in FIGS. 9-13, but can also act either alone or in combination with the camming means 234 to close the clip, such as a clip shown in FIG. 54 hereof. This particular clip 236 has a V-shaped configuration with a narrow end portion 236a which fits between pincers 239a and 239b. Thus, when the clip reaches the front end of the clip retaining cavity 205 and cannot move forward any further, added forward motion of the clip moving means 206 forces pincers 239a and 239b along the upper and lower surfaces of the clip 236 itself, thus effectively closure of the clip 236 between the pincers, with the clip then moving into slot 240 therebetween at the same time that it closes upon the target vessel 60. The rearward end 206b of the clip moving means 206 includes a transverse groove 224 extending therethrough. The clip moving means 206 is slidable between a retracted position remote from the clip retaining cavity 205 as shown in FIGS. 40 and 41, and a forward position proximate to the clip retaining cavity 205, as shown in FIG. 43. When the clip moving means 206 is in this forward position, the pincers 239a and 239b extend entirely into the clip retaining cavity 205 in the manner discussed above.

Figure 48:
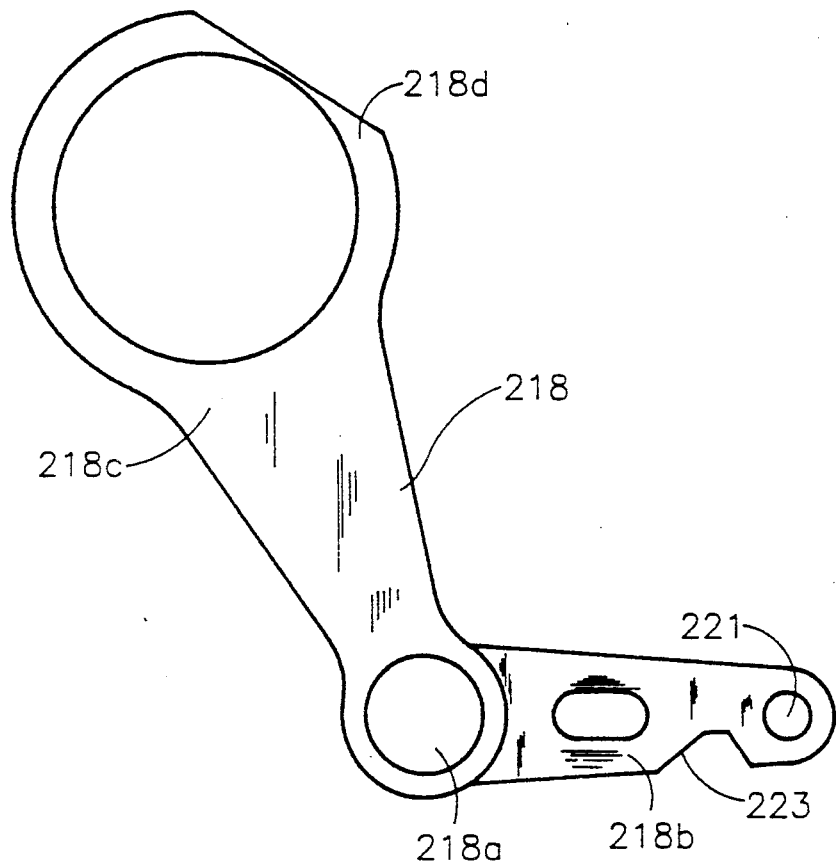
FIG. 48 is a top, elevational view of a handle member used in the apparatus shown in FIG. 40.
Figure 49:
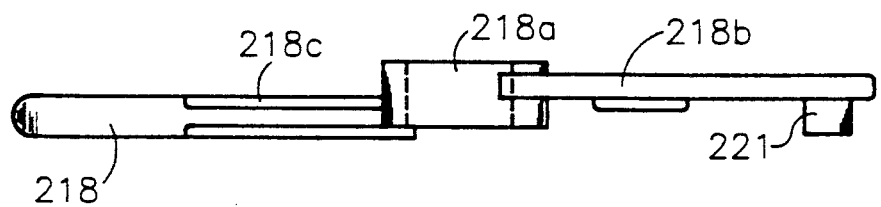
FIG. 49 is a side, elevational view of the handle shown in FIG. 48.

Movement of the clip moving means 206 between its forward and retracted positions is effected by the action of handle 218. Handle 218, which is specifically shown in FIGS. 48 and 49, is pivotally connected between housing portions 202a and 202b about pivot point 218a. This pivot point 218a includes a forward depending leg portion 218b angularly disposed with respect to rearward leg portion 218c which terminates in grip or finger hole 218d. Disposed at the forward portion 218b of the handle 218 is a projecting slot follower 221 which extends into slot 224. Thus, rotation of the handle 218 in a clockwise direction as shown in the Figures causes corresponding displacement of the forward portion 218b so that slot follower 221 moves upwardly within slot 224. However, since slot follower 221 is located below pivot point 218a, the motion of the slot follower 221 includes a forward longitudinal component directed towards jaws 203 and 204, thereby causing the clip moving means 206 to move forward into the clip retaining cavity 205. Conversely, counterclockwise rotation of handle 218 causes corresponding displacement of the forward portion 218b so that the slot follower 221 moves downwardly into slot 224, and the same time slot follower 221 provides a rearward longitudinal component directed away from the jaws 203 and 204, which causes clip moving means 206 to move away from the clip retaining cavity 205, and ultimately back to the position shown in FIGS. 40 and 41.

The device shown in FIGS. 40-43 also includes a number of safety features relating to the use of this device for the occlusion of various target vessels. Firstly, it is only possible to open the jaw members by rotating handle 217 into the position shown in FIG. 40 when the clip moving means 206 is in its rearward position as shown in FIGS. 40 and 41. Thus, handle 217 includes an extending L-shaped locking clamp 258a mounted on handle 217 by mounting bracket 260, as can best be seen in FIG. 42A. When handle 217 is thus in its closed position as shown in FIGS. 41-43, locking bracket 258a is in the position shown in FIG. 42A. At the same time, the rear portion 206c of the clip moving means 206 includes a lower extending L-shaped lip 206d extending outwardly from the plane of FIG. 41. When the clip moving means 206 has been moved forwardly in the manner discussed above into the position shown, for example, in FIGS. 42 and 43, rear portion 206c moves forwardly therewith, thus placing extending lip 206d below the inwardly extending L-shaped lip on bracket 258a (which extends downwardly into the plane of FIG. 41). These interlocking lips as shown in FIG. 42A thus prevent handle 217 from being rotated in a clockwise direction from the position shown in FIGS. 42 and 43. Attempting to move handle 217 in a clockwise direction thus results in interference between the inwardly extending lip of locking bracket 258a and the outwardly extending lip 206d so as to prevent such motion. To additionally stabilize the handle 217 in its closed position, toothed pawl 259 extends from handle 217 in the manner shown in FIG. 40. This toothed pawl operates in conjunction with a serrated face on housing portion 202a, as shown in FIG. 46. The teeth on the toothed pawl 259 thus engage the serrations on the serrated face of housing portion 202a, further locking the handle in its closed position. In order to open jaw 204 by pivotally rotating handle 217, if the clip moving means 206 is in its rearward position as in FIGS. 40 and 41, this can be accomplished merely by flexing handle 217 upwardly from the plane of the drawing in FIG. 46 so as to disengage the teeth of the pawl 259 from the serrations on the serrated face of the housing portion 202a, and then rotating handle 217 into the position shown in FIG. 40.

Provisions are also made in this device to prevent movement of the clip moving means 206 forward from the position shown in FIGS. 40 and 41 towards the clip retaining cavity 205. In particular, the forward portion 218b of handle 218 includes a slot 254 therein. In the inner portion of body portion 202a there is mounted a lock member 250, which can best be seen in FIGS. 40 and 41A. Lock member 250 is pivotally mounted upon pivot 256 and includes an upwardly extending lip 252, which can thus extend into slot 254. When this occurs in the manner shown in FIGS. 40 and 41A, it is not possible to rotate handle 218 from the position shown in FIG. 40 to the position shown in FIG. 43, since the upwardly extending lip 252 engages the outer perimeter of the slot 254 preventing further clockwise rotation thereof. It is therefore impossible to move clip moving means 206 towards clip retaining cavity 205 inadvertently. It is thus necessary to first release handle 218 by pivoting lock member 250 about pivot 256, so as to lower lip 252 out of slot 254. This is accomplished as follows, with specific reference to FIG. 41A. A nonlocking arcuate surface 254a at slot 254 on handle portion 218b permits counterclockwise rotation of handle 218 from the position shown in FIG. 41. This counterclockwise rotation, in turn, causes pivotal rotation of lock member 250 about pivot 256 by means of the camming action of handle portion 218b and arcuate surface 254a. This pivotal rotation is also counter to the spring action provided by flexible arm 250b of lock member 250, which tends to cause clockwise rotation of lock member 250 as shown in FIG. 41A, urging lip 252 into slot 254. In any event, when maximum counterclockwise rotation of lock member 250 is effected, the forward end 250a of lock member 250 latches under pawl hook 260a of catch mechanism 260, which thus prevents the reengagement of lip 252 into slot 254. This, in turn, permits free movement and clockwise rotation of handle 218.

In the operation of this device, a clip is introduced into the chamber, i.e., in front of clip moving means 206, when handle 218 is rotated into its fully counterclockwise position, as discussed above. As handle 218 is then rotated in a clockwise manner, the clip is then advanced to the front end of this device, until it reaches the clip retaining cavity 205, and is closed about the target vessel or tissue in the manner discussed above. The handle 218 will then be in its fully clockwise rotated position, and at this point the surface of handle portion 218b which includes notch 223 will now have contacted surface 260b as shown in FIG. 43, therefore flexing neck portion 206c and disengaging pawl hook 260a, and permitting re-engagement of lip 252 into slot 254. However, this cannot take place until the handle 218 returns to the position shown in FIG. 41.

Subsequent to capture of the target vessel 60 in the manner discussed above and as shown in FIGS. 40 and 41, the surgeon can thus effect movement of the clip moving means 206 so as to apply a clip to the target vessel in the manner discussed above.

Figure 53:
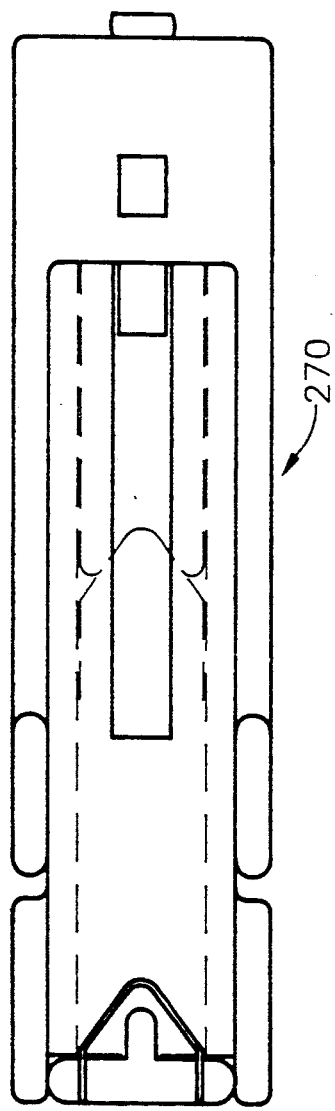
FIG. 53 is a top, elevational view of a clip-containing cartridge for use with the device shown in FIG. 40.
Figure 55:
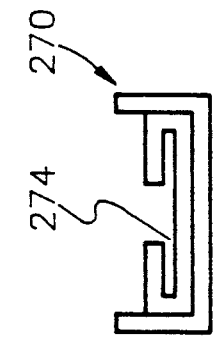
FIG. 55 is a side, sectional view of the cartridge shown in FIG. 53.
Figure 54:
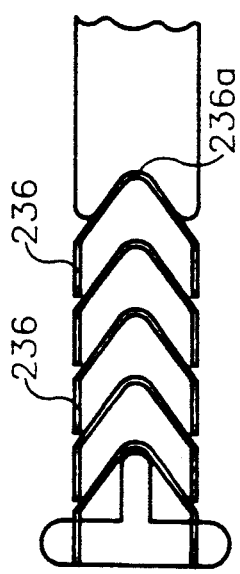
FIG. 54 is a representation of a series of clips contained within the cartridge device in FIG. 53.

Means are also provided for automatically and singularly placing clips in front of the clip moving means 206. These include a cartridge on the outer surface of the housing 202b, which cartridge assembly 270 is shown in FIG. 53. Cartridge assembly 270 is mounted on the external surface of housing portion 202b, and its forward portion extends through an opening in housing portion 202b ending at a location immediately forward of the clip moving means 206 when it is in its distal position with respect to clip retaining cavity 205, i.e., when it is in the position shown in FIGS. 40 and 41. Thus, when the clip moving means 206 is in this position, the cartridge 270 will automatically supply a clip forward of the clip moving means 206. However, when the clip moving means 206 then moves forward, it blocks the opening to cartridge 270, preventing any further clips from moving therethrough. After application of the clip, however, when the clip moving means 206 is again moved back into its distal position as shown in FIGS. 40 and 41, a further clip can then automatically be supplied thereto. Supply of the clips themselves from a series of clips as shown in FIG. 54 retained within the cartridge 270 is effected by the use of a spring mechanism at the rear end of the clips shown in FIG. 54, thus continuously urging clips 236 forwardly in the cartridge 270 towards the opening in the housing portion 202b. A cross-sectional view of the cartridge 270 is shown in FIG. 55, and shows a pathway 274 within which the clips can be slidably moved through the cartridge 270.

Subsequent to operation of the device in the manner discussed above, a clip 236 is left surrounding a target vessel 60 so as to occlude same. It is thus merely necessary to then return the clip moving means 206 from its forward position as shown in FIG. 43 to its distal position as shown in FIGS. 40 and 41 by rotating handle 218 in a counterclockwise direction, and then to open the jaws by rotating handle 217 downwardly so as to release the target vessel 60 with the clip 236 implanted thereon.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. Apparatus for implanting a closable clip to effect the occlusion of a target vessel or tissue, comprising first and second jaw members relatively movable between opened and closed positions, said first and second jaw members defining a clip-retaining cavity therebetween, said clip-retaining cavity having sufficient size to accommodate said clip therein, and clip closure means for moving said clip from a retractable position displaced from said clip-retaining cavity to an actuating position within said clip-retaining cavity, and for causing at least partial closure of said clip.

2. The apparatus of claim 1 including camming means disposed within said clip-retaining cavity for assisting in said at least partial closure of said clip.

3. The apparatus of claim 2 wherein said camming means is associated with at least one of said first and second jaw members.

4. The apparatus of claim 3 wherein said one of said first and second jaw members includes an inner surface defining a portion of said clip-retaining cavity, and wherein said camming means comprises an angularly displaced wall surface of said inner surface of said one of said first and second jaw members.

5. The apparatus of claim 1 wherein said clip closure means comprises a slidable pusher member including a first end proximate to said clip-retaining cavity and a second end distal from said clip-retaining cavity.

6. The apparatus of claim 5 wherein said clip closure means includes pivotable handle means including a first end distal from said second end of said slidable pusher member and a second end proximate to said second end of said slidable pusher member and in contact therewith, said pivotable handle means being pivotable about a point intermediate of said first and second ends of said pivotable handle means whereby pivoting of said pivotable handle means results in longitudinal displacement of said slidable pusher member.

7. The apparatus of claim 6 wherein said slidable pusher member includes groove means substantially transverse to the direction defined by said longitudinal displacement of said slidable pusher member, and wherein said pivotable handle means includes groove follower means.

8. The apparatus of claim 1 wherein said first jaw member remains stationary and said second jaw member is pivotable, including second jaw member pivot means for pivoting said second jaw member between said open and closed positions.

9. The apparatus of claim 8 wherein said second jaw pivot means comprises a second jaw handle member.

10. The apparatus of claim 9 including second handle member locking means for locking said second handle member in said closed position.

11. The apparatus of claim wherein said first and second jaw members define a smooth outer surface.

12. The apparatus of claim 11 wherein said first and second jaw members combine to define an opening at the distal end therebetween, said opening substantially duplicating the occlusion of said target vessel or tissue by said clip when said clip is closed.

* * * * *

UNITED STATES PATENT AND TRADEMARK OFFICE
CERTIFICATE OF CORRECTION

PATENT NO. : 5,067,958

DATED : November 26, 1991

INVENTOR(S) : Jeffrey J. Sandhaus

It is certified that error appears in the above-identified patent and that said Letters Patent is hereby corrected as shown below:

Column 1, line 38, following "that" insert --a--.
Column 18, line 32, "extendinq" should read --extending--.
Column 20, line 54, following "claim" insert --1--.

Signed and Sealed this

Thirtieth Day of March, 1993

Attest:

STEPHEN G. KUNIN

*Attesting Officer*   *Acting Commissioner of Patents and Trademarks*